United States Patent
Kono et al.

(10) Patent No.: US 10,194,783 B2
(45) Date of Patent: Feb. 5, 2019

(54) IMAGE PROCESSING APPARATUS, IMAGE PROCESSING METHOD, AND COMPUTER-READABLE RECORDING MEDIUM FOR DETERMINING ABNORMAL REGION BASED ON EXTENSION INFORMATION INDICATING STATE OF BLOOD VESSEL REGION EXTENDING IN NEIGHBORHOOD OF CANDIDATE REGION

(71) Applicant: OLYMPUS CORPORATION, Tokyo (JP)

(72) Inventors: Takashi Kono, Hachioji (JP); Yamato Kanda, Hino (JP); Masashi Hirota, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 68 days.

(21) Appl. No.: 15/402,369

(22) Filed: Jan. 10, 2017

(65) Prior Publication Data
US 2017/0112357 A1    Apr. 27, 2017

Related U.S. Application Data

(63) Continuation of application No. PCT/JP2015/069344, filed on Jul. 3, 2015.

(30) Foreign Application Priority Data

Jul. 15, 2014 (JP) ................................. 2014-145154

(51) Int. Cl.
*G06K 9/00* (2006.01)
*A61B 1/00* (2006.01)
(Continued)

(52) U.S. Cl.
CPC ...... *A61B 1/00009* (2013.01); *A61B 1/00039* (2013.01); *A61B 1/04* (2013.01); *A61B 1/045* (2013.01); *A61B 1/3137* (2013.01)

(58) Field of Classification Search
None
See application file for complete search history.

(56) References Cited

U.S. PATENT DOCUMENTS

| | | | |
|---|---|---|---|
| 4,961,110 A | 10/1990 | Nakamura | |
| 8,837,821 B2 | 9/2014 | Hirota et al. | |
| 2014/0275995 A1* | 9/2014 | Sheehan | A61B 1/3137 600/424 |

FOREIGN PATENT DOCUMENTS

| | | |
|---|---|---|
| JP | H02-224635 A | 9/1990 |
| JP | 2918162 A | 7/1999 |

(Continued)

OTHER PUBLICATIONS

International Search Report dated Sep. 8, 2015 issued in PCT/JP2015/069344.
English Abstract of JP H02-124131 A, filed May 11, 1990.

*Primary Examiner* — Idowu O Osifade
(74) *Attorney, Agent, or Firm* — Scully, Scott, Murphy & Presser, P.C.

(57) ABSTRACT

An image processing apparatus includes: a blood vessel sharpness image creation unit configured to create a blood vessel sharpness image representing sharpness of a blood vessel region in which a blood vessel is shown in an intraluminal image; an abnormal candidate region extraction unit configured to extract a region in which the sharpness is decreased in the blood vessel sharpness image, as a candidate region for an abnormal region in which a visible vascular pattern is locally lost; and an abnormal region determination unit configured to determine whether the candidate region is an abnormal region, based on extension (Continued)

information indicating a state of the blood vessel region extending in a neighborhood of the candidate region.

15 Claims, 20 Drawing Sheets

(51) Int. Cl.
*A61B 1/04* (2006.01)
*A61B 1/045* (2006.01)
*A61B 1/313* (2006.01)

(56) References Cited

FOREIGN PATENT DOCUMENTS

| | | |
|---|---|---|
| JP | 2918162 B2 | 7/1999 |
| JP | 2005-192880 A | 7/2005 |
| JP | 2008-029520 A | 2/2008 |
| JP | 2011-234931 A | 11/2011 |

\* cited by examiner

FIG.13
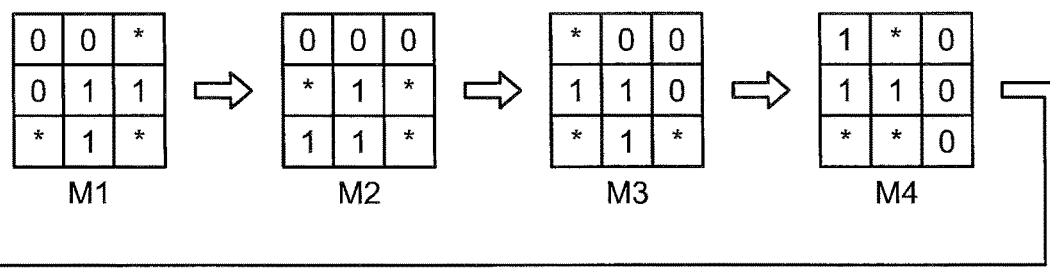
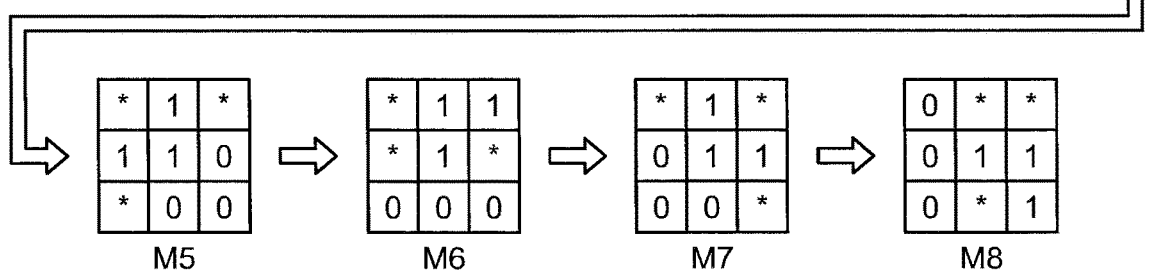

SI=0

SI=0.25

SI=0.5

SI=0.75

SI=1.0

IMAGE PROCESSING APPARATUS, IMAGE PROCESSING METHOD, AND COMPUTER-READABLE RECORDING MEDIUM FOR DETERMINING ABNORMAL REGION BASED ON EXTENSION INFORMATION INDICATING STATE OF BLOOD VESSEL REGION EXTENDING IN NEIGHBORHOOD OF CANDIDATE REGION

CROSS REFERENCES TO RELATED APPLICATIONS

This application is a continuation of PCT international application Ser. No. PCT/JP2015/069344, filed on Jul. 3, 2015 which designates the United States, incorporated herein by reference, and which claims the benefit of priority from Japanese Patent Application No. 2014-145154, filed on Jul. 15, 2014, incorporated herein by reference.

BACKGROUND

1. Technical Field

The disclosure relates to an image processing apparatus, an image processing method, and a computer-readable recording medium, for performing image processing on an intraluminal image of a living body.

2. Related Art

There is a known technique of detecting an abnormal region including an image of an abnormal portion such as a tumor, on an image obtained by imaging the inside of a lumen of a living body, using a medical observation device such as an endoscope and a capsule endoscope. Hereinafter, an image obtained by imaging the inside of a lumen will also be referred to as an intraluminal image. For example, JP 2008-29520 A discloses a technique to detect a lesion having a locally raised shape. JP 2008-29520 A estimates a three-dimensional model based on a two-dimensional image of a living tissue, sets a detection target region for a lesion having a raised shape, for the three-dimensional model, calculates shape feature data representing a state of a shape on each of data points included in the detection target region, and detects a lesion having a locally raised shape based on the shape feature data. JP 2005-192880 A discloses a technique of first calculating feature data by performing spatial frequency analysis using a Gabor filter, or the like, on an image of a G-component, among red (R), green (G), and blue (B) components, and thereafter, discriminating abnormality based on a state in which a blood vessel extends, by applying a linear discriminant function. The state in which the blood vessel extends is also referred to as a blood vessel running state.

SUMMARY

In some embodiments, an image processing apparatus includes: a blood vessel sharpness image creation unit configured to create a blood vessel sharpness image representing sharpness of a blood vessel region in which a blood vessel is shown in an intraluminal image; an abnormal candidate region extraction unit configured to extract a region in which the sharpness is decreased in the blood vessel sharpness image, as a candidate region for an abnormal region in which a visible vascular pattern is locally lost; and an abnormal region determination unit configured to determine whether the candidate region is an abnormal region, based on extension information indicating a state of the blood vessel region extending in a neighborhood of the candidate region.

In some embodiments, an image processing method includes: creating a blood vessel sharpness image representing sharpness of a blood vessel region in which a blood vessel is shown in an intraluminal image; extracting a region in which the sharpness is decreased in the blood vessel sharpness image, as a candidate region for an abnormal region in which a visible vascular pattern is locally lost; and determining whether the candidate region is an abnormal region, based on extension information indicating a state of the blood vessel region extending in a neighborhood of the candidate region.

In some embodiments, provided is a non-transitory computer-readable recording medium with an executable program stored thereon. The program causes a computer to execute: creating a blood vessel sharpness image representing sharpness of a blood vessel region in which a blood vessel is shown in an intraluminal image; extracting a region in which the sharpness is decreased in the blood vessel sharpness image, as a candidate region for an abnormal region in which a visible vascular pattern is locally lost; and determining whether the candidate region is an abnormal region, based on extension information indicating a state of the blood vessel region extending in a neighborhood of the candidate region.

The above and other features, advantages and technical and industrial significance of this invention will be better understood by reading the following detailed description of presently preferred embodiments of the invention, when considered in connection with the accompanying drawings.

BRIEF DESCRIPTION OF THE DRAWINGS

FIG. 13 is a schematic diagram for illustrating thinning processing;

DETAILED DESCRIPTION

Hereinafter, an image processing apparatus, an image processing method, and an image processing program, according to embodiments of the present invention will be described with reference to the drawings. The present invention is not limited by these embodiments. The same reference signs are used to designate the same elements throughout the drawings.

First Embodiment

Figure 1:
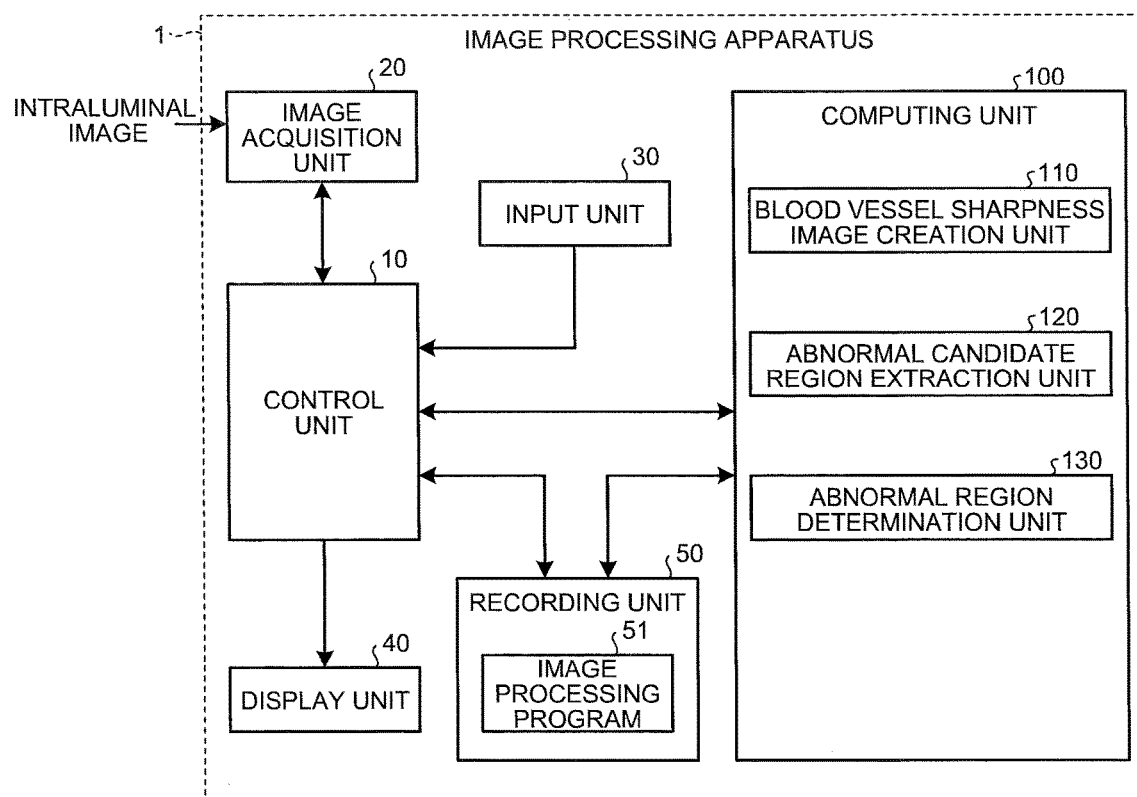
FIG. 1 is a block diagram illustrating a configuration of an image processing apparatus according to a first embodiment of the present invention.

FIG. 1 is a block diagram illustrating a configuration of an image processing apparatus according to a first embodiment of the present invention. An image processing apparatus 1 according to the first embodiment is an apparatus configured to detect a region suspected to be a neoplastic lesion as an abnormal region, from an intraluminal image, by performing image processing on an intraluminal image obtained by imaging the inside of a lumen of a living body using a medical imaging device such as an endoscope. The typical intraluminal image is a color image having a pixel level (pixel value) for a wavelength component of each of R (red), G (green), and B (blue) at each of pixel positions.

As illustrated in FIG. 1, the image processing apparatus 1 includes a control unit 10, an image acquisition unit 20, an input unit 30, a display unit 40, a recording unit 50, and a computing unit 100. The control unit 10 controls general operation of the image processing apparatus 1. The image acquisition unit 20 obtains image data generated by the medical observation device that has imaged the inside of a lumen. The input unit 30 inputs a signal corresponding to operation from the outside, into the control unit 10. The display unit 40 displays various types of information and images. The recording unit 50 stores image data obtained by the image acquisition unit 20, and various programs. The computing unit 100 executes predetermined image processing on the image data.

The control unit 10 is implemented by hardware such as a CPU. The control unit 10 integrally controls general operation of the image processing apparatus 1, specifically, reads various programs recorded in the recording unit 50 and thereby transmitting instruction and data to individual sections constituting the image processing apparatus 1 in accordance with image data input from the image acquisition unit 20 and with signals, or the like, input from the input unit 30.

The image acquisition unit 20 is configured appropriately in accordance with system modes including a medical imaging device. For example, in a case where the medical imaging device is connected to the image processing apparatus 1, the image acquisition unit 20 is configured with an interface for incorporating image data generated by the medical imaging device. In another case of installing a server for saving image data generated by the medical imaging device, the image acquisition unit 20 is configured with a communication device, or the like, connected with the server, and obtains image data by performing data communication with the server. Alternatively, the image data generated by the medical imaging device may be transmitted via a portable recording medium. In this case, the portable recording medium is removably attached to the image acquisition unit 20, which is configured with a reader device to read image data of the recorded image.

The input unit 30 is implemented with input devices such as a keyboard, a mouse, a touch panel, and various switches and outputs input signals generated in response to the external operation for these input devices, to the control unit 10.

The display unit 40 is implemented with display devices such as an LCD and an EL display and displays various screens including an intraluminal image, under the control of the control unit 10.

The recording unit 50 is implemented with various IC memories such as ROM and RAM including an updatable flash memory, a hard disk that is built in or connected via a data communication terminal, information recording device such as a CD-ROM and its reading device, or the like. The recording unit 50 stores image data of the intraluminal image obtained by the image acquisition unit 20, programs for operating the image processing apparatus 1 and for causing the image processing apparatus 1 to execute various functions, data to be used during execution of this program, or the like. Specifically, the recording unit 50 stores an image processing program 51 that extracts a region in which a visible vascular pattern is locally lost, from an intraluminal image, as an abnormal region, and a threshold, or the like, to be used in the image processing.

The computing unit 100 is implemented with hardware such as a CPU. The computing unit 100 executes image processing of extracting, from an intraluminal image, a region in which the visible vascular pattern is locally lost, as an abnormal region, by reading the image processing program 51.

Next, the configuration of the computing unit 100 will be described. As illustrated in FIG. 1, the computing unit 100 includes a blood vessel sharpness image creation unit 110, an abnormal candidate region extraction unit 120, and an abnormal region determination unit 130. The blood vessel sharpness image creation unit 110 calculates sharpness (hereinafter, referred to as a blood vessel sharpness) of a blood vessel region that is a region in which a blood vessel existing on a mucosa surface is shown, among the intraluminal image, and creates a blood vessel sharpness image in which the blood vessel sharpness is defined as luminance. The abnormal candidate region extraction unit 120 extracts, on the blood vessel sharpness image, a region in which blood vessel sharpness is decreased, as a candidate region for an abnormal region. The abnormal region determination unit 130 determines whether the candidate region is the abnormal region on the basis of extension information on the blood vessel region existing in the neighborhood of the candidate region.

A blood vessel existing in the neighborhood of the surface of the mucosa is seen through, by observation of the inside of a lumen. An image of such a blood vessel is referred to as a visible vascular pattern. The blood vessel sharpness is a level indicating how the visible vascular pattern looks in vividness, clarity, and the level of contrast. In the first embodiment, blood vessel sharpness is set such that the greater the vividness of the visible vascular pattern, the larger the value becomes. Specifically, the amount corresponding to an absorbance change amount inside a lumen is defined as the blood vessel sharpness. In addition, in the description, "locally lost" represents any of "locally difficult to see" and "locally completely invisible".

Figure 2:
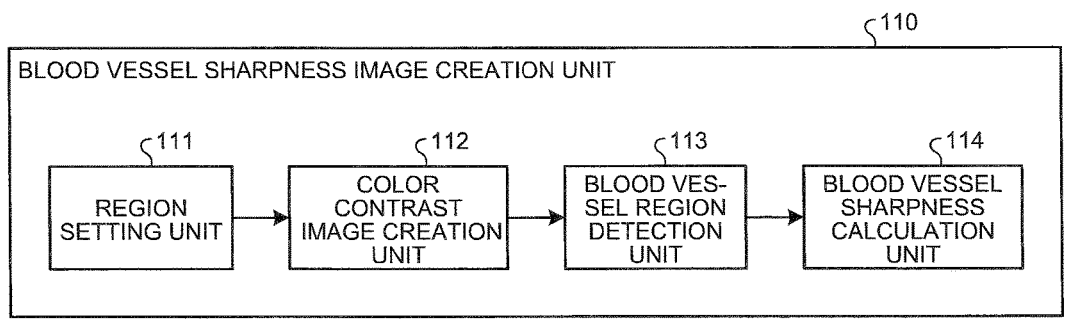
FIG. 2 is a block diagram illustrating a detailed configuration of a blood vessel sharpness image creation unit illustrated in FIG. 1.

FIG. 2 is a block diagram illustrating a detailed configuration of the blood vessel sharpness image creation unit 110 illustrated in FIG. 1. As illustrated in FIG. 2, the blood vessel sharpness image creation unit 110 includes a region setting unit 111, a color contrast image creation unit 112, a blood vessel region detection unit 113, and a blood vessel sharpness calculation unit 114. The region setting unit 111 sets a region to be a detection target for the abnormal region, specifically, a mucosa region, among the intraluminal image. The color contrast image creation unit 112 creates a color contrast image for the region set by the region setting unit 111. The blood vessel region detection unit 113 detects a blood vessel region on the basis of a luminance change on the color contrast image. The blood vessel sharpness calculation unit 114 calculates feature data representing the shape of the luminance change in the blood vessel region, as blood vessel sharpness.

The region setting unit 111 sets a region obtained by eliminating a region in which at least any of a mucosa contour, a dark portion, specular reflection, a bubble, and a residue is shown, from the intraluminal image, as a detection target region of an abnormal region, namely, as a mucosa region.

The color contrast image creation unit 112 creates a color contrast image, in which the more the absorbance for hemoglobin absorption wavelength band, for example, a wavelength band in the neighborhood of 530 to 550 nm, in a region within the lumen, that is, the more reddish in the region on the intraluminal image, the more the luminance decreases for the region.

Figure 3:
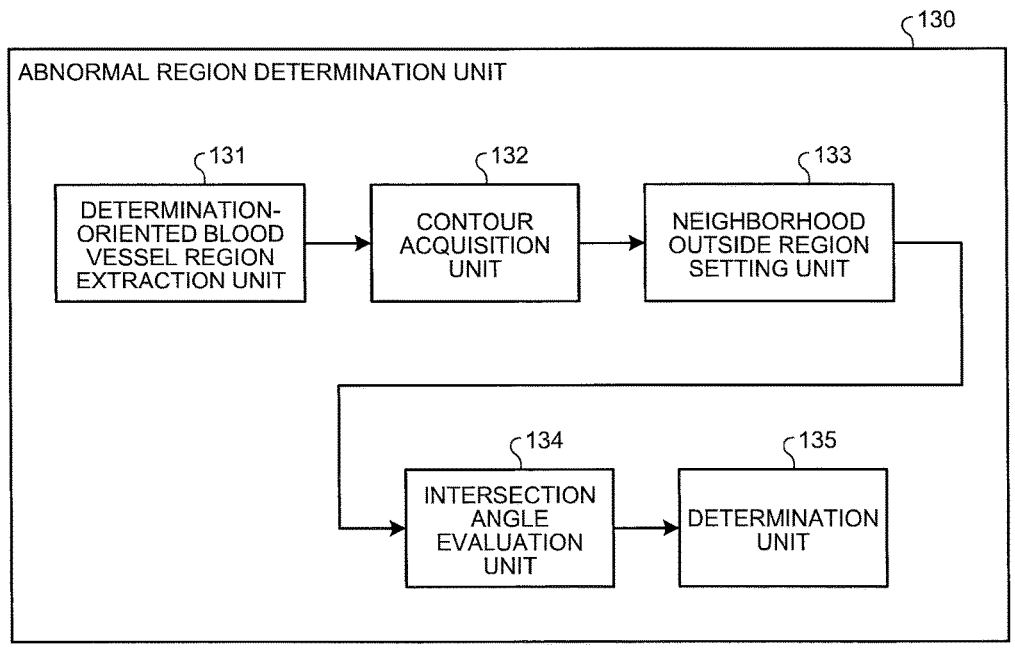
FIG. 3 is a block diagram illustrating a detailed configuration of an abnormal region determination unit illustrated in FIG. 1.

FIG. 3 is a block diagram illustrating a detailed configuration of the abnormal region determination unit 130 illustrated in FIG. 1. As illustrated in FIG. 3, the abnormal region determination unit 130 includes a determination-oriented blood vessel region extraction unit 131, a contour acquisition unit 132, a neighborhood outside region setting unit 133, an intersection angle evaluation unit 134, and a determination unit 135. The determination-oriented blood vessel region extraction unit 131 extracts a blood vessel region to be used for determining whether the candidate region is an abnormal region, from the intraluminal image. The contour acquisition unit 132 obtains a contour of the candidate region. The neighborhood outside region setting unit 133 sets a region outside of the contour of the candidate region, as a neighborhood outside region. The intersection angle evaluation unit 134 evaluates an intersection angle between the blood vessel region existing in the neighborhood outside region, and the contour of the candidate region. The determination unit 135 determines whether the candidate region is the abnormal region on the basis of a result of evaluation performed by the intersection angle evaluation unit 134.

Figure 4:
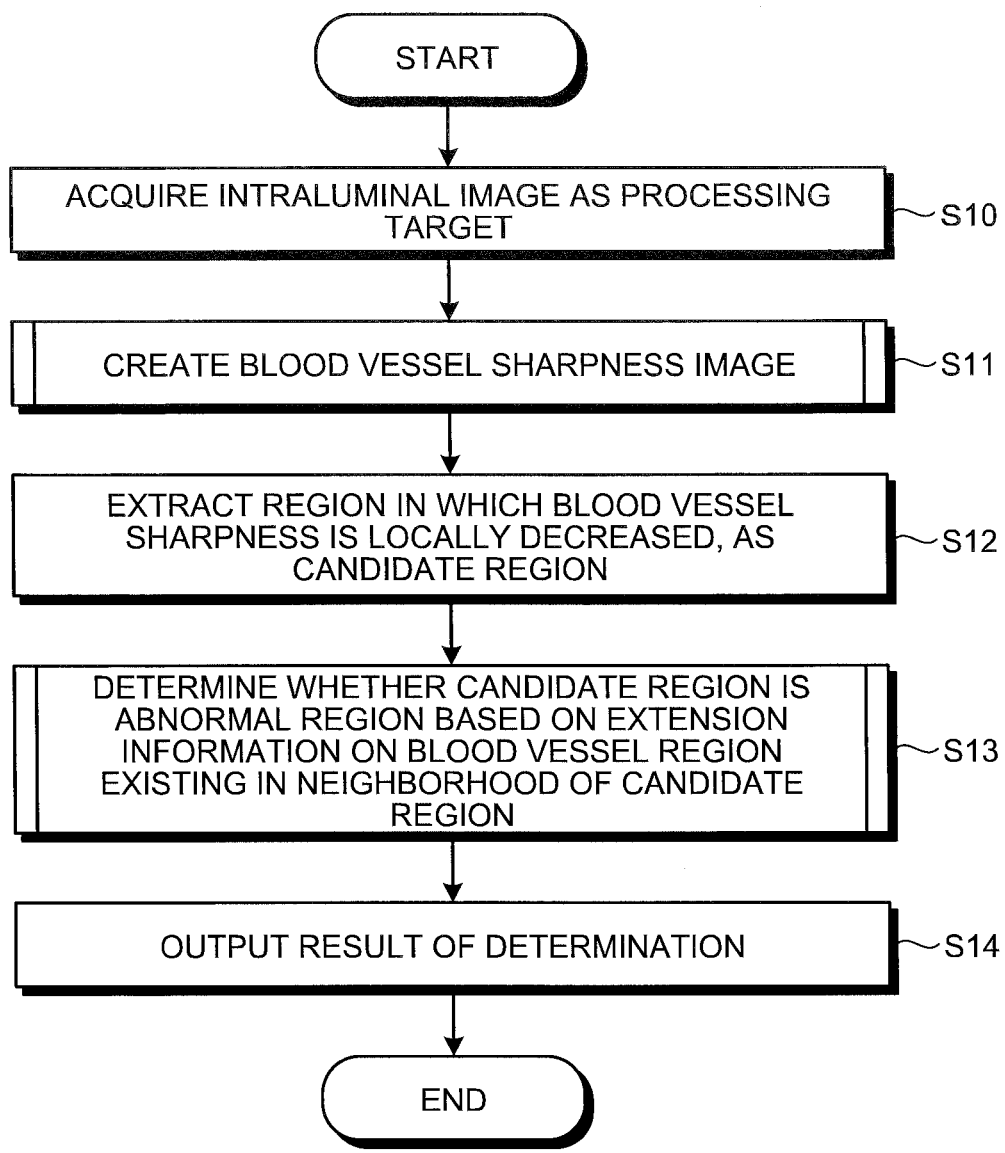
FIG. 4 is a flowchart illustrating operation of the image processing apparatus illustrated in FIG. 1.
Figure 5:
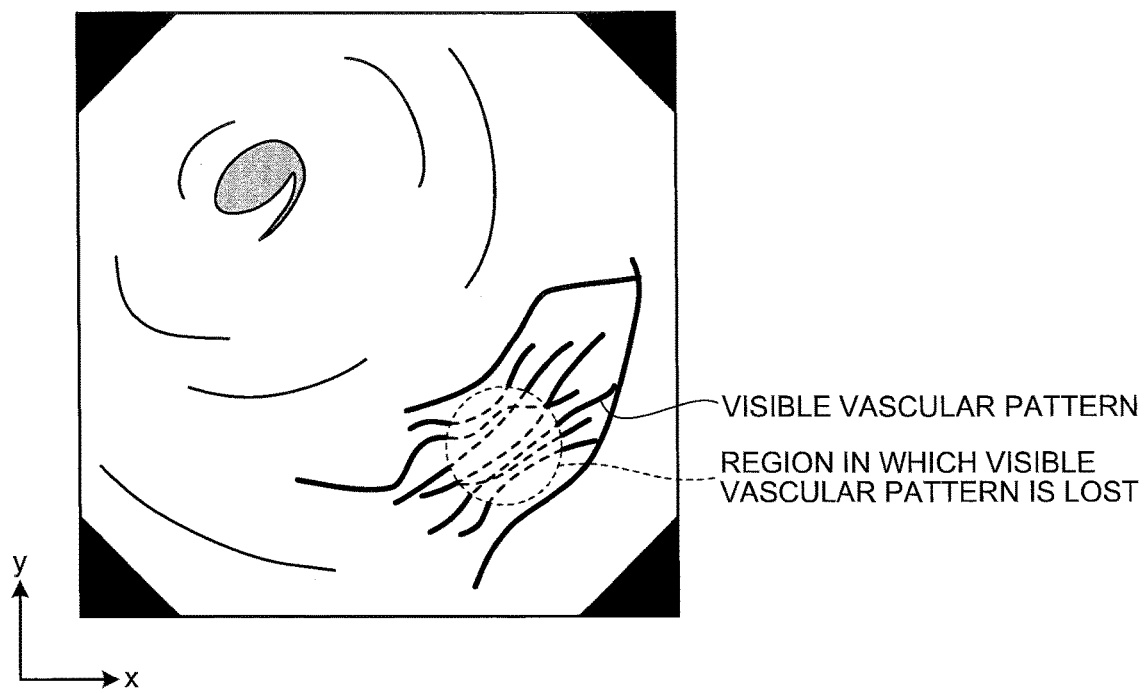
FIG. 5 is a schematic diagram illustrating an exemplary intraluminal image.

Next, operation of the image processing apparatus 1 will be described. FIG. 4 is a flowchart illustrating operation of the image processing apparatus 1. First, in step S10, the image processing apparatus 1 acquires an intraluminal image via the image acquisition unit 20. In the first embodiment, an intraluminal image is generated by imaging in which illumination light (white light) including wavelength components of R, G, and B is emitted inside a lumen using an endoscope. The intraluminal image has pixel values (R-value, G-value, and B-value) that correspond to these wavelength components on individual pixel positions. FIG. 5 is a schematic diagram illustrating an exemplary intraluminal image obtained in step S10. As illustrated in FIG. 5, a region in which a visible vascular pattern is partially difficult to see is a region in which the visible vascular pattern is lost.

Figure 6:
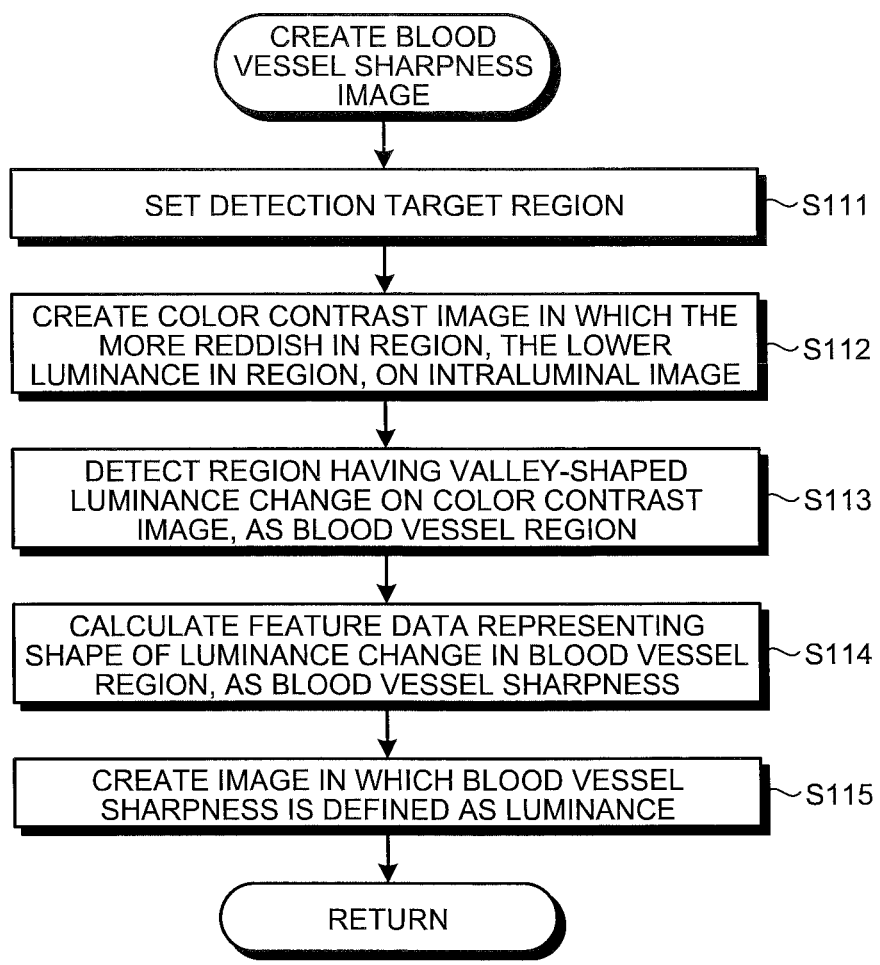
FIG. 6 is a flowchart illustrating processing of creating a blood vessel sharpness image, executed by the blood vessel sharpness image creation unit illustrated in FIG. 1.

In subsequent step S11, the computing unit 100 incorporates the intraluminal image and creates a blood vessel sharpness image on the basis of the intraluminal image. FIG. 6 is a flowchart illustrating processing of creating a blood vessel sharpness image, executed by the blood vessel sharpness image creation unit 110.

In step S111, the region setting unit 111 sets a region obtained by eliminating a region in which any of a mucosa contour, a dark portion, specular reflection, a bubble, and a residue is shown, from the intraluminal image, that is, sets a mucosa region, as a detection target region of an abnormal region. Specifically, the region setting unit 111 calculates a G/R-value for each of the pixels within the intraluminal image, and sets a region having the G/R-value equal to or less than a discriminating threshold for discriminating mucosa region, that is, a reddish region, as a detection target region.

The method for setting the detection target region is not limited to the above-described method, and thus various known methods may be applied. For example, as disclosed in JP 2007-313119 A, it is allowable to detect a bubble region by detecting a match between a bubble model to be set on the basis of a characteristic of a bubble image, such as an arc-shaped protruding edge due to illumination reflection, existing at a contour portion of a bubble or inside the bubble, with an edge extracted from the intraluminal image. As disclosed in JP 2011-234931 A, it is allowable to extract a black region on the basis of color feature data based on each of the pixel values (R-value, G-value, and B-value) and to determine whether the black region is a dark portion on the basis of the direction of the pixel value change around this black region. Alternatively, it is allowable to extract a white region on the basis of color feature data based on each of the pixel values and to determine whether the white region is a specular reflection region on the basis of the pixel value change around a boundary of the white region. Further alternatively, as disclosed in JP 2012-143340 A, it is allowable to detect a residue candidate region, that is assumed to be a non-mucosa region, on the basis of color feature data based on each of the pixel values and to determine whether the residue candidate region is a mucosa region on the basis of the positional relationship between the residue candidate region and the edge extracted from the intraluminal image.

In subsequent step S112, the color contrast image creation unit 112 creates a color contrast image in which the more reddish in a region, the lower the luminance in the region, on the intraluminal image. As specific processing, the color contrast image creation unit 112 calculates a G/R value obtained by dividing the G-value that corresponds to a wavelength component in the neighborhood of 530 to 550 nm as hemoglobin absorption wavelength band, by the R-value, among pixel values (R-value, G-value, and B-value) of each of pixels within the intraluminal image. The R-component of the illumination light used in imaging the inside of a lumen corresponds to a wavelength band with very little absorption for hemoglobin. Accordingly, the attenuation amount of the R-component inside of the lumen corresponds to the distance for which the illumination light travels through the inside of the lumen. Therefore, the G/R value can be considered as a value obtained by normalizing the hemoglobin absorbance wavelength component corresponding to the G-value by an imaging distance, that is, a distance from an imaging unit included in the endoscope, or the like, to the mucosa surface. The color contrast image creation unit 112 creates a color contrast image in which this G/R value is defined as luminance.

In subsequent step S113, the blood vessel region detection unit 113 detects a region having a valley-shaped luminance change on the color contrast image, as a blood vessel region. As specific processing, the blood vessel region detection unit 113 first sets a pixel-of-interest in a detection target region (refer to step S111) within the color contrast image. Subsequently, using the luminance of the pixel-of-interest and the luminance of a neighborhood pixel of the pixel-of-interest, an eigenvalue $\lambda$ that satisfies a matrix equation represented by formula (2) is calculated with respect to the Hessian matrix given by formula (1).

$$H(x_0, y_0) = \begin{pmatrix} \frac{\partial^2 I(x_0, y_0)}{\partial x^2} & \frac{\partial^2 I(x_0, y_0)}{\partial x \partial y} \\ \frac{\partial^2 I(x_0, y_0)}{\partial y \partial x} & \frac{\partial^2 I(x_0, y_0)}{\partial y^2} \end{pmatrix} \quad (1)$$

$$|H - \lambda E| = 0 \quad (2)$$

The value $I(x_0, y_0)$ in formula (1) represents the luminance of the pixel-of-interest positioned on coordinates $(x_0, y_0)$ within the color contrast image. The sign E in formula (2) represents an identity matrix.

When a three-dimensional space including a pixel x-y coordinates and luminance (z-coordinate) on the color contrast image is assumed, the luminance change is represented by the shape of a two-dimensional curved surface (x, y, z). Regarding a point $(x_0, y_0, z)$ on the two-dimensional curved surface, a point $(x_0, y_0, z)$ on the two-dimensional curved surface in which the direction having a maximum slope on the neighborhood pixel represents a recess-shaped slope and the direction orthogonal to the direction represents a flat slope, is considered to be a valley-shape. In the first embodiment, among the eigenvalue $\lambda$ of the Hessian matrix, that satisfies formula (2), an eigenvalue (first eigenvalue) $\lambda_{max}$ having a larger absolute value represents the curvature in a direction where the slope becomes maximum on the point $(x_0, y_0, z)$ on the two-dimensional curved surface, that corresponds to the pixel-of-interest. In contrast, an eigenvalue (second eigenvalue) $\lambda_{min}$, having a smaller absolute value represents the curvature in a direction orthogonal to the direction in which the slope becomes maximum on the same point $(x_0, y_0, z)$. Accordingly, when the sign of the curvature (first eigenvalue $\lambda_{max}$) in the direction in which the slope is the maximum is negative, and when the curvature (second eigenvalue $\lambda_{min}$) in the direction orthogonal to the direction in which the slope is the maximum is close to zero, it is possible to determine that the shape of the two-dimensional curved surface, namely, the luminance change, is valley-shaped.

Figure 7:
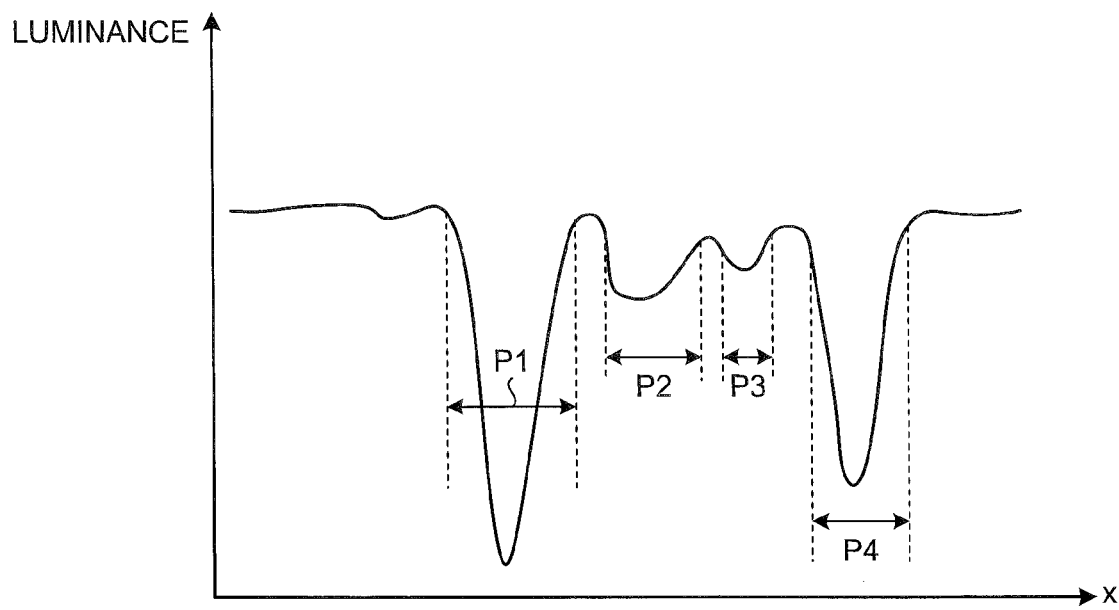
FIG. 7 is a graph illustrating a luminance change in the x-direction within a color contrast image.

The blood vessel region detection unit 113 detects a region in which the luminance change is valley-shaped on the color contrast image, as a blood vessel region, on the basis of the first eigenvalue $\lambda_{max}$ and the second eigenvalue $\lambda_{min}$ of the Hessian matrix, calculated for each of the pixels within the color contrast image. FIG. 7 is a graph illustrating a luminance change in one direction (x-direction) within a color contrast image. In the case of FIG. 7, regions P1 to P4 are extracted as blood vessel regions, for example.

In subsequent step S114, the blood vessel sharpness calculation unit 114 calculates feature data representing the shape of luminance change in the blood vessel region detected in step S113, as blood vessel sharpness. Specifically, using the first eigenvalue $\lambda_{max}$ and the second eigenvalue $\lambda_{min}$ of the Hessian matrix in the blood vessel region, an evaluation value CV (curvedness) given by the following formula (3) is calculated, and this evaluation value CV is defined as blood vessel sharpness. Note that, while the first embodiment calculates the evaluation value CV as the blood vessel sharpness, the present invention is not limited to this. It is also allowable to calculate the blood vessel sharpness using known methods such as the modulation transfer function (MTF) and the contrast transfer function (CTF).

$$CV = \sqrt{\frac{\lambda_{max}^2 - \lambda_{min}^2}{2}} \quad (3)$$

The evaluation value CV changes such that the sharper the curve, that is, the steeper the luminance change, the greater the value. In the case of FIG. 7, for example, the evaluation value CV calculated for each of the regions P1 and P4 is greater than the evaluation value CV calculated for each of the regions P2 and P3, respectively.

Figure 8:
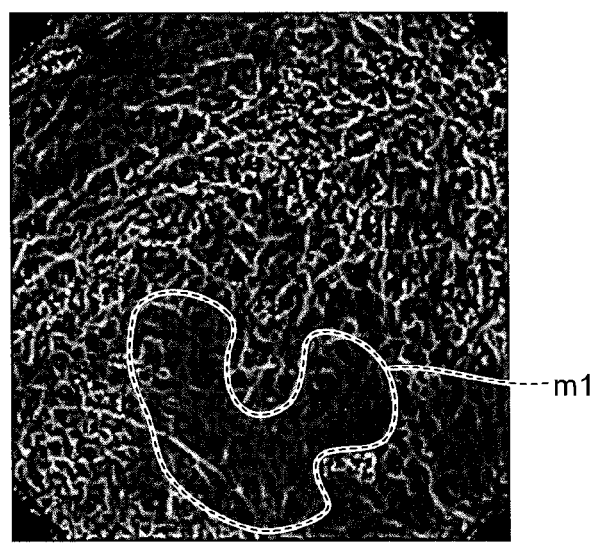
FIG. 8 is a diagram illustrating an exemplary blood vessel sharpness image.

In subsequent step S115, the blood vessel sharpness image creation unit 110 creates an image in which the blood vessel sharpness calculated in step S114 is defined as luminance. Hereinafter, the image in which blood vessel sharpness is defined as luminance is referred to as a blood vessel sharpness image. FIG. 8 is a diagram illustrating an exemplary blood vessel sharpness image. Thereafter, operation of the computing unit 100 returns to the main routine.

Figure 9:
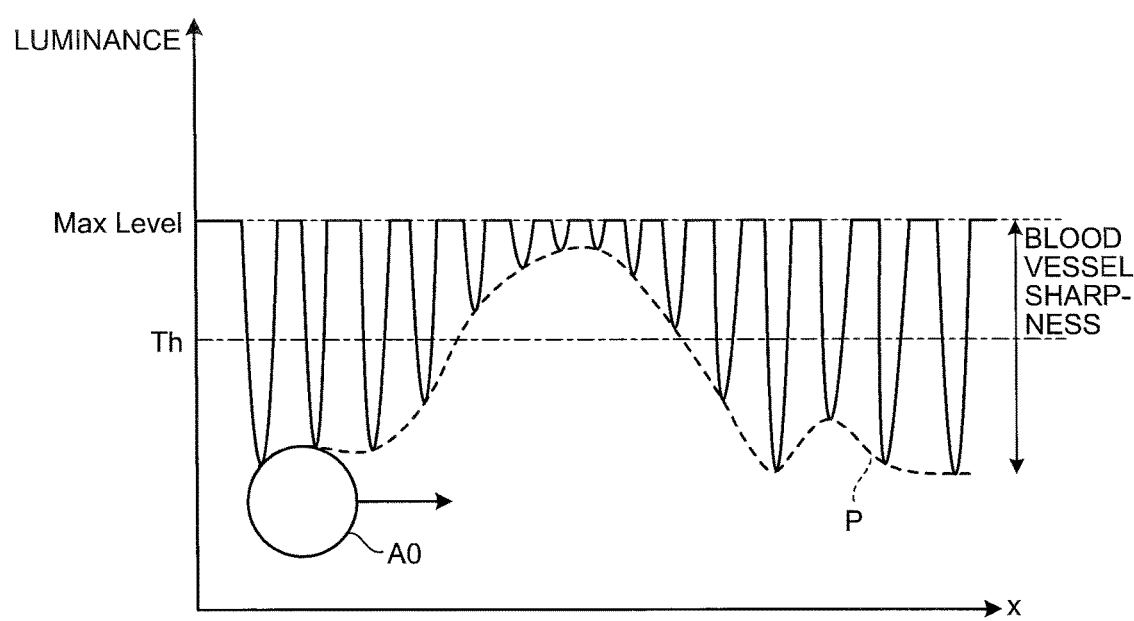
FIG. 9 is a graph illustrating a luminance change in the x-direction on a reversed image of a blood vessel sharpness image.

In step S12 subsequent to step S11, the abnormal candidate region extraction unit 120 extracts a region in which blood vessel sharpness is locally decreased, as a candidate region for an abnormal region. As specific processing, the abnormal candidate region extraction unit 120 first creates a reversed image obtained by reversing luminance of the blood vessel sharpness image and performs shading morphology processing, that is, morphology processing for a gray-scale image, on the reversed image for each of detection target regions (refer to step S111 in FIG. 6). FIG. 9 is a graph illustrating a luminance change in one direction (x-direction) on a reversed image of a blood vessel sharpness image. By performing closing processing of morphology on the luminance change using a structural element A0, it is possible to obtain a reference surface P in which the luminance change is smoothed. Note that, FIG. 9 illustrates a shape of the reference surface P in the x-direction. Smoothing of luminance may also be performed on the reversed image by performing low-pass filter processing instead of closing processing.

Subsequently, the abnormal candidate region extraction unit 120 performs threshold processing using a preset threshold Th on the reference surface P, thereby creating a binary image. On this binary image, a region having luminance, specifically, a region having luminance of the threshold Th or above in FIG. 9 corresponds to the region in which blood vessel sharpness has been locally decreased. The abnormal candidate region extraction unit 120 further performs particle analysis on this binary image and excludes a region having the circularity below a predetermined threshold, that is, a region that is not like a circle, and a region having the area smaller than a predetermined threshold, as noise, and then, extracts an ultimately remaining region as a candidate region. In FIG. 8, a candidate region m1 extracted in this manner is displayed being superposed onto the blood vessel sharpness image.

Figure 10:
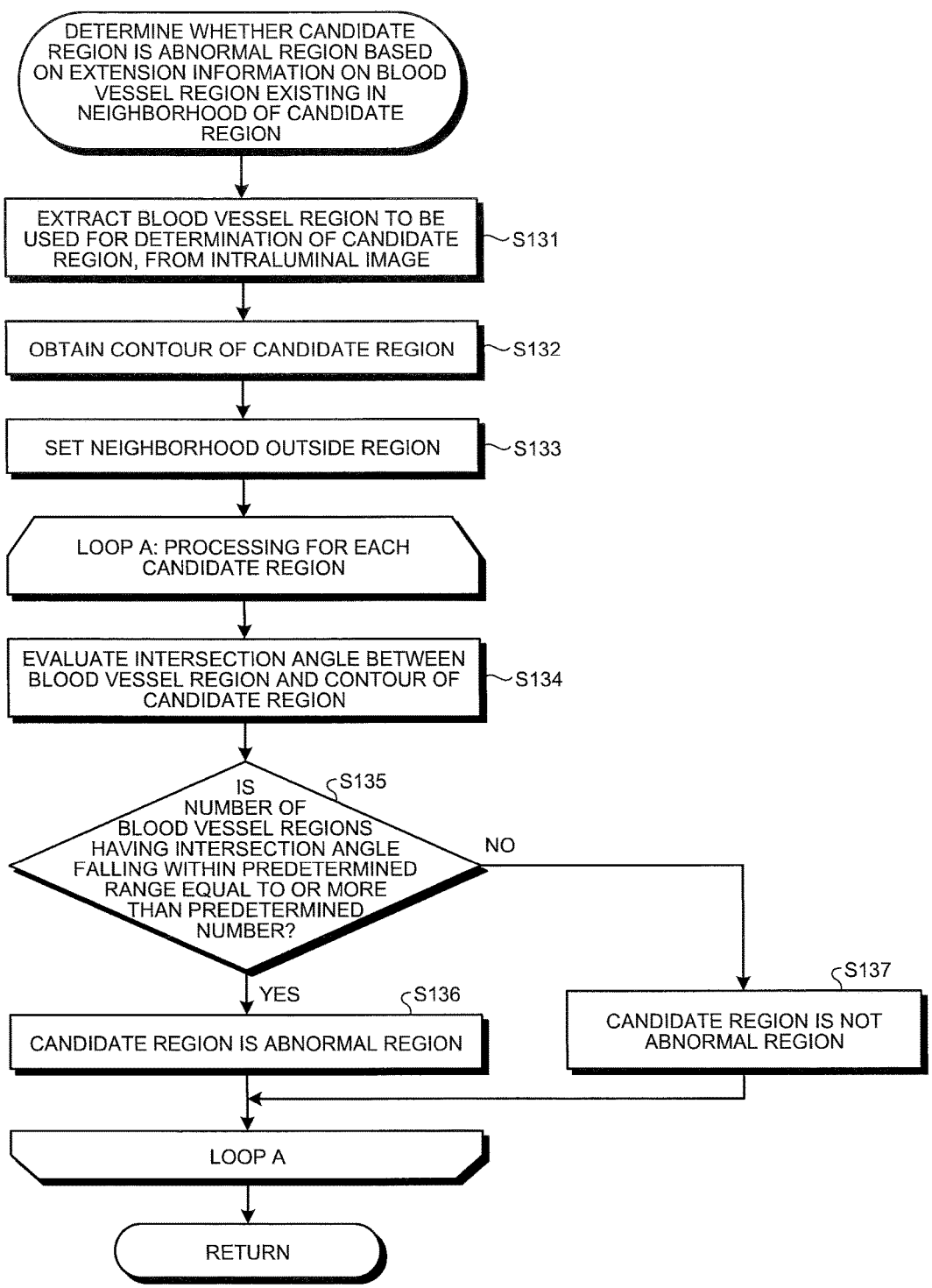
FIG. 10 is a flowchart illustrating processing of determining a candidate region, executed by the abnormal region determination unit illustrated in FIG. 1.

In subsequent step S13, the abnormal region determination unit 130 determines whether the candidate region is the abnormal region on the basis of extension information on the blood vessel region in the neighborhood of the candidate region. The extension information on the blood vessel region is information indicating a state how the blood vessel region extends around the candidate region. In the first embodiment, the number of blood vessel regions intersecting at an intersection angle having a predetermined range with respect to the contour of the candidate region is used as the extension information on the blood vessel region. FIG. 10 is a flowchart illustrating processing of determining a candidate region, executed by the abnormal region determination unit 130.

First, in step S131, the determination-oriented blood vessel region extraction unit 131 extracts, from the intraluminal image, a blood vessel region to be used for determination of the candidate region, that is, a region having a valley-shaped luminance change on the color contrast image. As specific processing, it is allowable to obtain the blood vessel region detected by the blood vessel region detection unit 113 from the blood vessel sharpness image creation unit 110, or to restart extracting blood vessel regions similarly to steps S111 to S113 in FIG. 6.

In subsequent step S132, the contour acquisition unit 132 performs edge extraction processing using a differential filter, or the like, on the binary image created in step S12, thereby obtaining the contour of the candidate region.

Figure 11A:
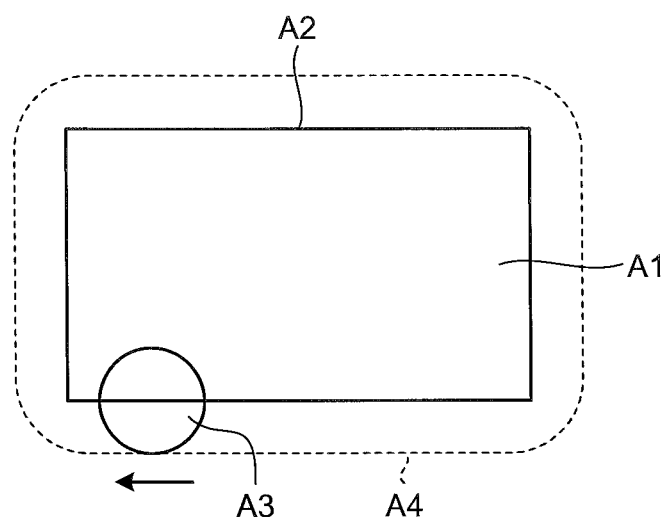
FIGS. 11A and 11B are schematic diagrams for illustrating processing of setting a neighborhood outside region.
Figure 11B:
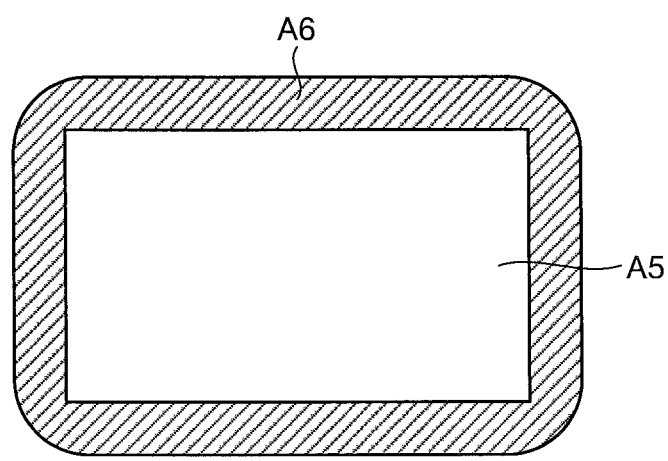

In subsequent step S133, the neighborhood outside region setting unit 133 sets a predetermined range of region outside of the contour of the candidate region, as a neighborhood outside region. The neighborhood outside region is an evaluation region used in determination of the candidate region. FIGS. 11A and 11B are schematic diagrams for illustrating processing of setting the neighborhood outside region.

As specific processing, the neighborhood outside region setting unit 133 executes labeling processing (reference: "Digital image processing" (p. 181), Computer Graphic Arts (CG-ARTS) Society) on the binary image created in step S12, thereby giving label number to each of the candidate regions. Then, morphology processing (reference: "Morphology" (p. 12, p. 43), CORONA PUBLISHING CO., LTD.) is performed for each of the label numbers. Specifically, as illustrated in FIG. 11A, a Minkowski sum region A4 is obtained by applying a circular structural element A3 along a contour A2 of a candidate region A1. Subsequently, as illustrated in FIG. 11B, a region A6 is extracted by subtracting, from the Minkowski sum region A4, a closing region A5, that is, a region obtained by performing closing processing of morphology on the candidate region A1. The neighborhood outside region setting unit 133 sets this region A6 as a neighborhood outside region.

The diameter of the structural element A3 may be set as a fixed value, or may be set such that the smaller the imaging distance, the larger the diameter of the structural element A3 on the basis of the imaging distance (refer to step S112) in the candidate region. The size (width) of the region A6 as the neighborhood outside region varies with the diameter of the structural element A3.

Figure 12A:
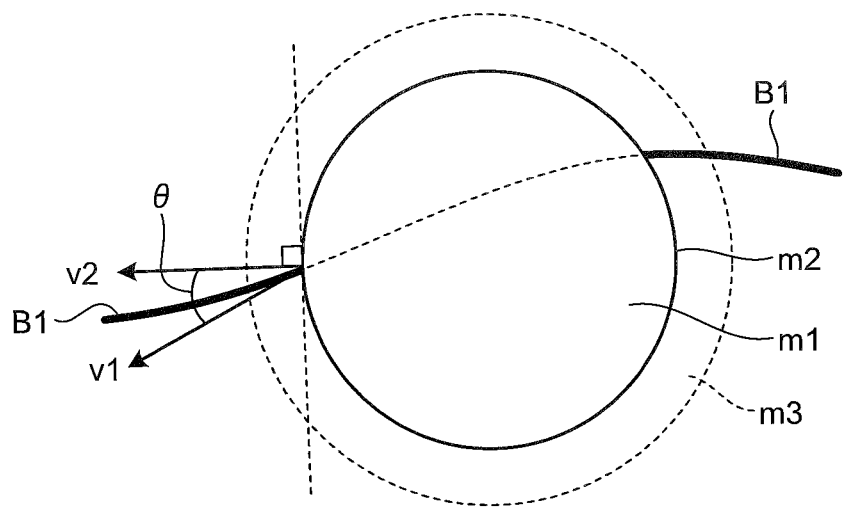
FIGS. 12A and 12B are schematic diagrams for illustrating a method of evaluating an intersection angle between a blood vessel region and a contour of a candidate region.
Figure 12B:
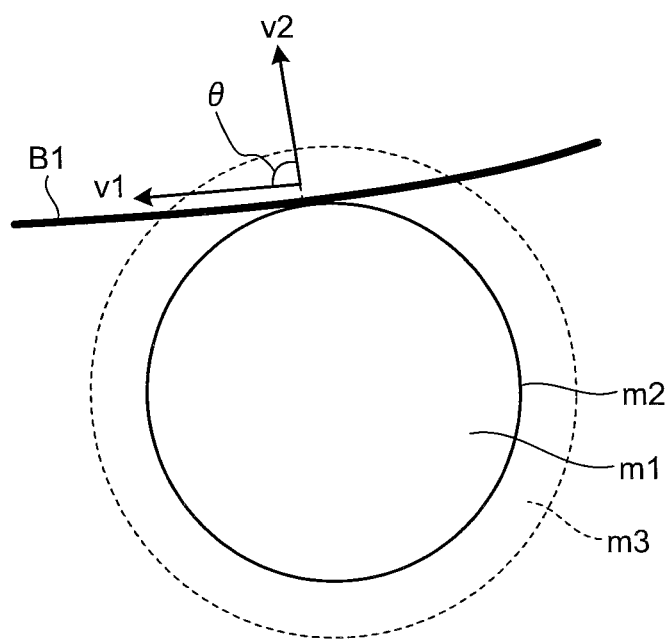
Figure 14A:
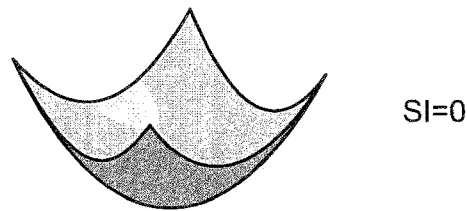
FIGS. 14A to 14E are schematic diagrams illustrating a shape model corresponding to a shape index value.
Figure 14B:
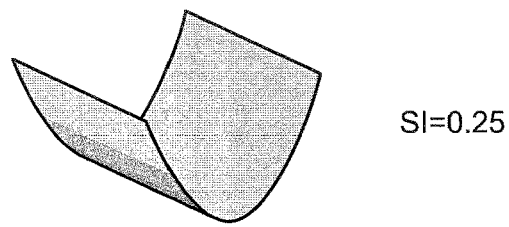
Figure 14C:
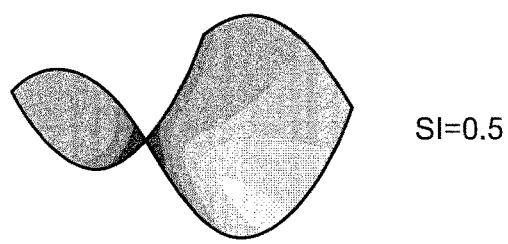
Figure 14D:
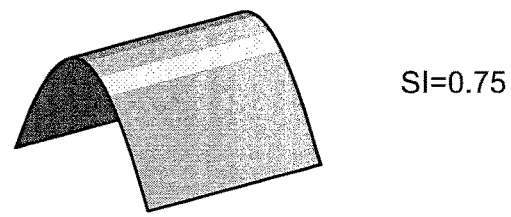
Figure 14E:
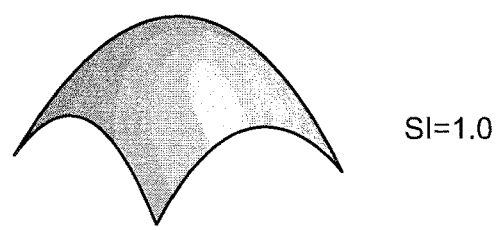

Subsequently, the abnormal region determination unit 130 executes loop-A processing for each of the candidate regions to which label numbers have been given. In step S134, the intersection angle evaluation unit 134 evaluates an intersection angle between the blood vessel region and the contour of the candidate region. This evaluation is executed for each of the blood vessel regions included in the neighborhood outside region of the candidate region as a processing target, among the blood vessel regions extracted in step S131. FIGS. 12A and 12B are schematic diagrams for illustrating a method of evaluating an intersection angle between a blood vessel region and a contour of a candidate region.

As illustrated in FIGS. 12A and 12B, the intersection angle evaluation unit 134 performs thinning processing on each of the blood vessel regions existing in a neighborhood outside region m3, thereby extracting a thin blood vessel B1. FIG. 13 is a schematic diagram for illustrating thinning processing of the blood vessel region. The thin blood vessel B1 can be extracted by the procedure including creating a binary image by performing binarization processing on the neighborhood outside region m3 and repeating processing of sequentially searching local region patterns M1 to M8 each formed with 3×3 pixels, illustrated in FIG. 13, and processing of deleting a central pixel from the binary image (reference: "Image Analysis Handbook" pp 577 to 578, University of Tokyo Press). Specifically, the pattern M1 is searched from the binary image and the pixel value of the central pixel of the region that matches the pattern M1 is changed to zero. The mark * illustrated in FIG. 13 represents a pixel that need not be considered. Next, the pattern M2 is searched from the binary image and the pixel value of the central pixel of the region that matches the pattern M2 is changed to zero. This processing is repeated up to the pattern M8, forming one cycle. This cycle is repeated until there is no more point to delete.

The intersection angle evaluation unit 134 obtains a directional vector v1 of the thin blood vessel B1 at an intersection between the thin blood vessel B1 extracted in this manner, and a contour m2 of the candidate region m1. Note that the directional vector v1 may be obtained as an average of directional vectors on several pixels on the thin blood vessel B1 in the neighborhood of the intersection with the contour m2.

Moreover, the intersection angle evaluation unit 134 obtains a normal vector v2 for a tangent of the contour m2 at the intersection between the thin blood vessel B1 and the contour m2. Note that the normal vector v2 may be obtained as an average of normal vectors on several pixels on the contour m2 in the neighborhood of the intersection with the thin blood vessel B1.

The intersection angle evaluation unit 134 evaluates whether an intersection angle $\theta$ between the directional vector v1 and the normal vector v2 is within a predetermined range. As illustrated in FIG. 12A, in a case where the intersection angle $\theta$ is relatively small, that is, close to 0°, it is highly possible that the thin blood vessel B1 existing in the neighborhood outside region m3 intersects with contour m2 and penetrates into the candidate region m1. As illustrated in FIG. 12B, in a case where the intersection angle θ is close to ±90°, it is highly possible that the thin blood vessel B1 extends along the contour m2 of the candidate region m1.

In step S135, the determination unit 135 determines whether the number of blood vessel regions having the intersection angle θ falling within a predetermined range, for example, |θ|≤45°, is equal to or more than a predetermined number. If the number of blood vessel regions having the intersection angle θ falling within the predetermined range is equal to or more than the predetermined number (step S135: Yes), the determination unit 135 determines that the candidate region m1 as a processing target is the abnormal region (step S136). In contrast, if the number of blood vessel regions having the intersection angle θ falling within the predetermined range is less than the predetermined number (step S135: No), the determination unit 135 determines that the candidate region m1 as a processing target is not the abnormal region (step S137).

After the loop-A processing has been performed for all the extracted candidate regions, operation of the computing unit 100 returns to the main routine.

In step S14 subsequent to step S13, the computing unit 100 outputs a determination result of step S13. In response to this, the control unit 10 displays the region determined as an abnormal region, onto the display unit 40. The method for displaying the region determined as an abnormal region is not particularly limited. An exemplary method would be to superpose a mark indicating the region determined as an abnormal region, onto the intraluminal image and to display the region determined to be an abnormal region in a color different from other regions, or with shading. Together with this, the determination result on the abnormal region in step S13 may be recorded on the recording unit 50. Thereafter, operation of the image processing apparatus 1 is finished.

As described above, according to the first embodiment of the present invention, the blood vessel sharpness image representing blood vessel sharpness on the intraluminal image is created, a region in which blood vessel sharpness is locally decreased is extracted as a candidate region for an abnormal region, and whether the candidate region is the abnormal region is determined on the basis of the number of blood vessel regions intersecting at an intersection angle having a predetermined range with respect to the candidate region, as the extension information on the blood vessel region. As a result, it is possible to detect the abnormal region with high accuracy.

Modification 1-1

Next, modification 1-1 of the first embodiment of the present invention will be described. When a blood vessel region is detected from a color contrast image (refer to step S113 in FIG. 6), it is allowable to use a shape index calculated from an eigenvalue of the Hessian matrix. Specifically, a shape index SI is given by the following formula (4) using a first eigenvalue $\lambda_{max}$ and a second eigenvalue $\lambda_{min}$ of the Hessian matrix.

$$SI = \frac{1}{2} - \frac{1}{\pi}\arctan\frac{\lambda_{max} + \lambda_{min}}{\lambda_{max} - \lambda_{min}} \quad (4)$$

The shape index SI has a value ranging from 0 to 1. FIGS. 14A to 14E are schematic diagrams illustrating a shape model corresponding to the value of the shape index SI. From this, in a case where a region having a valley-shaped luminance change on the color contrast image is to be detected as a blood vessel region, it would be sufficient to detect a region having the shape index SI ranging 0≤SI≤0.5.

Modification 1-2

Next, modification 1-2 of the first embodiment of the present invention will be described. When a blood vessel region is detected from a color contrast image (refer to step S113 in FIG. 6), it is allowable to use a specific spatial frequency. Specifically, a spatial frequency band region having a specific range is extracted by performing high-pass filter processing (reference: Digital image processing" (p. 135), Computer Graphic Arts (CG-ARTS) Society) on the color contrast image, and this extracted region is determined as a blood vessel region.

Modification 1-3

Next, modification 1-3 of the first embodiment of the present invention will be described. While in the first embodiment, the intersection angle for each of all blood vessel regions existing in the neighborhood outside region with respect to the contour of the candidate region is evaluated, it is allowable to restrict, to some degree, the thickness of the blood vessel region as an evaluation target. For example, it is allowable to perform the above-described evaluation selectively on the blood vessel having a predetermined thickness or above. In this case, it would be sufficient to extract a blood vessel region having a thickness corresponding to a filter by performing band-pass filter processing on the neighborhood outside region, and to evaluate the intersection angle with respect to the contour of the candidate region, for the extracted blood vessel region.

Modification 1-4

Next, modification 1-4 of the first embodiment of the present invention will be described. In a case, as illustrated in modification 1-3, where processing is performed by restricting the thickness of the blood vessel region as the evaluation target, it is allowable to set the size of the structural element used in morphology processing at setting of the neighborhood outside region, in accordance with the thickness of the blood vessel region. Specifically, it would be preferable to set such that, the thicker the blood vessel region, the greater the size of the structural element.

Modification 1-5

Next, modification 1-5 of the first embodiment of the present invention will be described. In the above-described first embodiment, the angle θ (refer to FIGS. 12A and 12B) between the directional vector v1 of the thin blood vessel B1 and the normal vector v2 for the tangent of the contour m2 is used as the intersection angle between the blood vessel region and the contour of the candidate region. Alternatively, it is allowable to use an angle θ' (θ'=90°−θ) between the directional vector v1 and the tangent of the contour m2, as the intersection angle. In this case, the more closer to 90°, for example, in a range of 45°≤θ'≤135°, the angle θ', the higher the possibility of blood vessel region being intersecting the contour m2 of the candidate region m1 and being penetrating into the candidate region.

Modification 1-6

Next, modification 1-6 of the first embodiment of the present invention will be described. Determination of whether the candidate region is the abnormal region (refer to FIG. 10) may be performed on the basis of the extension information on the blood vessel region, other than the intersection angle θ. For example, it is possible to use the length of the blood vessel region in the neighborhood outside region.

As specific processing, thinning processing is first performed on the neighborhood outside region and the blood vessel region existing outside of the neighborhood outside region, and thus, the thin blood vessel existing on the outer contour of the neighborhood outside region is extracted. Subsequently, a thin blood vessel is tracked within the neighborhood outside region by searching 8-neighbor pixels on the thin blood vessel, starting from the outer contour of the neighborhood outside region. Subsequently, the tracking is finished at a point where the thin blood vessel reaches an inner contour of the neighborhood outside region, and the length of the thin blood vessel B1 in the neighborhood outside region is calculated. In practice, the number of pixels is counted as the length. If the length is equal to or less than a predetermined threshold, it is more likely that the thin blood vessel B1 intersects the contour m2 and penetrate into the candidate region m1. Accordingly, if the predetermined number or more of the blood vessel regions (thin blood vessel B1) having the length equal to or less than the predetermined threshold exists in the neighborhood outside region, it is possible to determine that the candidate region is the abnormal region.

Modification 1-7

Next, modification 1-7 of the first embodiment of the present invention will be described. In the above-described first embodiment, whether the candidate region is the abnormal region is determined on the basis of the number of blood vessel regions in which the intersection angle θ is within a predetermined range. However, the determination method is not limited to this. For example, determination may be performed on the basis of the ratio of the blood vessel regions in which the intersection angle θ is within a predetermined range. For example, in a case where the number of blood vessel regions in which the intersection angle θ is within a predetermined range corresponds to 50% or above, with respect to the number of blood vessel regions existing in the neighborhood outside region, it is determined that the candidate region is the abnormal region.

Second Embodiment

Figure 15:
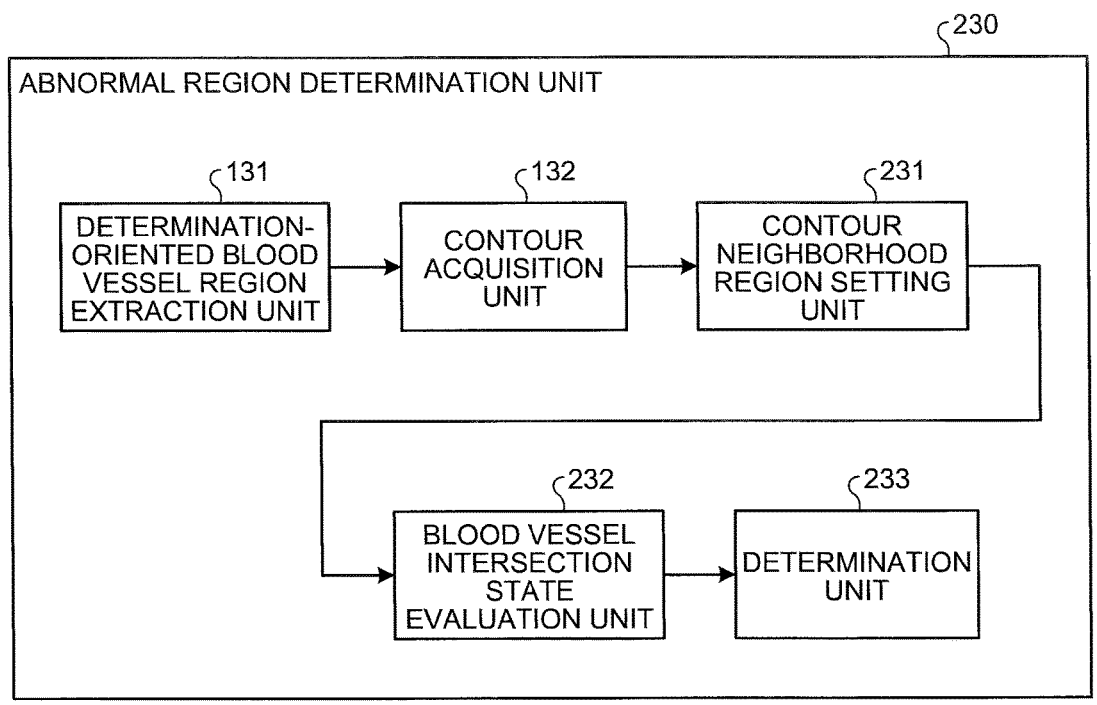
FIG. 15 is a block diagram illustrating a configuration of an abnormal region determination unit included in an image processing apparatus according to a second embodiment.

Next, a second embodiment of the present invention will be described. FIG. 15 is a block diagram illustrating a configuration of an abnormal region determination unit included in an image processing apparatus according to the second embodiment. The image processing apparatus according to the second embodiment includes an abnormal region determination unit 230 illustrated in FIG. 15 instead of the abnormal region determination unit 130 illustrated in FIG. 1 Configurations and operation of each of the units in the image processing apparatus are similar to the case of the first embodiment, except for the abnormal region determination unit 230.

The abnormal region determination unit 230 includes a determination-oriented blood vessel region extraction unit 131, a contour acquisition unit 132, a contour neighborhood region setting unit 231, a blood vessel intersection state evaluation unit 232, and a determination unit 233. The determination-oriented blood vessel region extraction unit 131 extracts, from the intraluminal image, a blood vessel region to be used for determining whether the candidate region is an abnormal region. The contour acquisition unit 132 obtains a contour of the candidate region. The contour neighborhood region setting unit 231 sets a region on the outside and inside of the contour of the candidate region, as a contour neighborhood region. The blood vessel intersection state evaluation unit 232 evaluates the intersection state of the blood vessel region with respect to the candidate region, in the contour neighborhood region. The determination unit 233 determines whether the candidate region is the abnormal region on the basis of a result of evaluation performed by the blood vessel intersection state evaluation unit 232. Operation of the determination-oriented blood vessel region extraction unit 131 and the contour acquisition unit 132 are similar to the case of the first embodiment.

Next, operation of the image processing apparatus according to the second embodiment will be described. General operation of the image processing apparatus according to the second embodiment is similar to the case of the first embodiment (refer to FIG. 4), except for a difference in details of determination processing on the candidate region in step S13, from the first embodiment. In the second embodiment, the number of blood vessel regions that intersect the contour of the candidate region and penetrate into the candidate region is used as the extension information on the blood vessel region.

Figure 16:
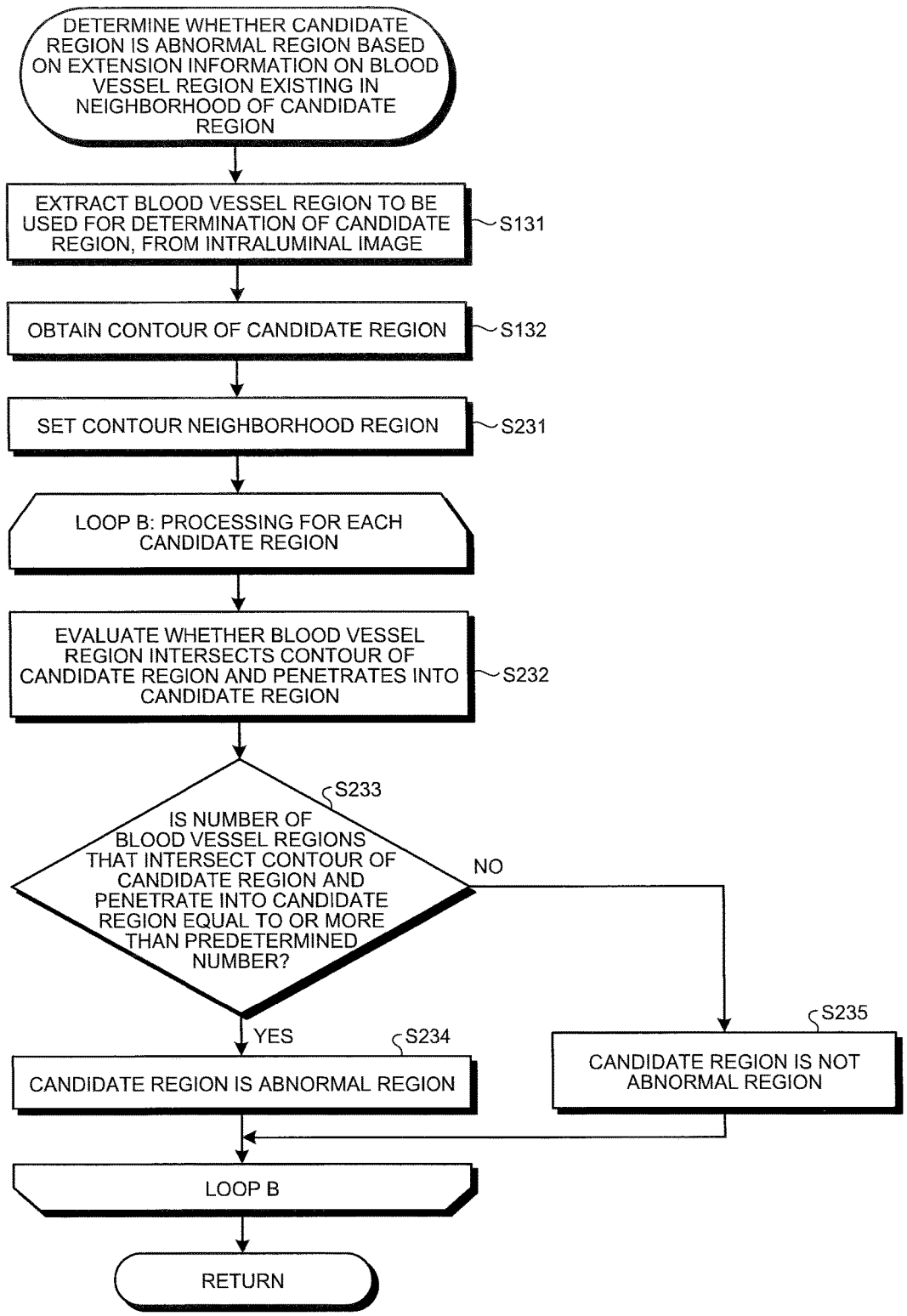
FIG. 16 is a flowchart illustrating processing of determining a candidate region, executed by the abnormal region determination unit illustrated in FIG. 15.

FIG. 16 is a flowchart illustrating processing of determining a candidate region, executed by the abnormal region determination unit 230 in step S13 illustrated in FIG. 4. Note that steps S131 and S132 illustrated in FIG. 16 are similar to the steps in the first embodiment.

Figure 17A:
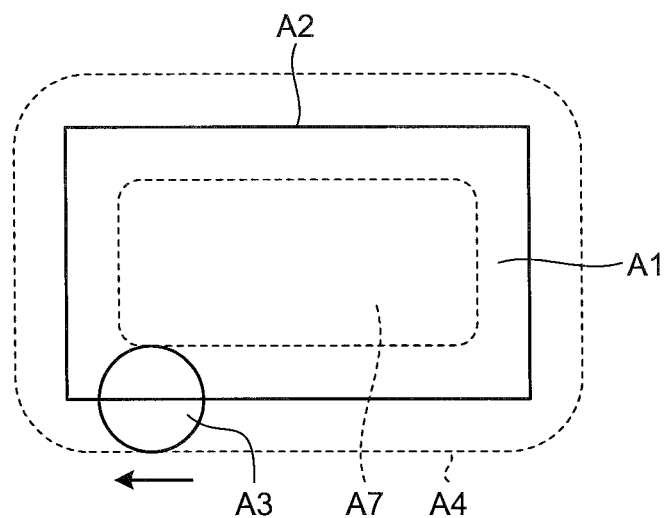
FIGS. 17A and 17B are schematic diagrams for illustrating processing of setting a contour neighborhood region.
Figure 17B:
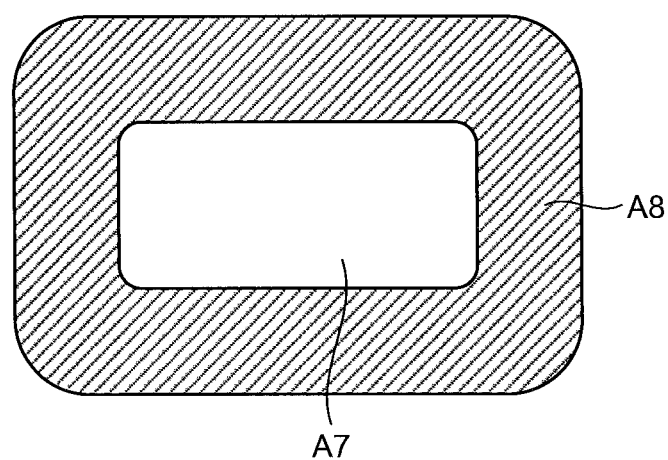

In step S231 subsequent to step S132, the contour neighborhood region setting unit 231 sets a predetermined range of region outside and inside the contour of the candidate region, as a contour neighborhood region. The contour neighborhood region is an evaluation region used in determination of the candidate region. FIGS. 17A and 17B are schematic diagrams for illustrating processing of setting a contour neighborhood region.

As specific processing, the contour neighborhood region setting unit 231 executes labeling processing (reference: "Digital image processing" (p. 181), Computer Graphic Arts (CG-ARTS) Society) on the binary image created in step S12, thereby giving label number to each of the candidate regions. Then, morphology processing (reference: "Morphology" (p. 12, p. 43), CORONA PUBLISHING CO., LTD.) is performed for each of the label numbers. Specifically, as illustrated in FIG. 17A, the Minkowski sum region A4 and a Minkowski difference region A7 are obtained by applying the circular structural element A3 along the contour A2 of the candidate region A1. Subsequently, a region A8 is extracted by subtracting Minkowski difference region A7 from the Minkowski sum region A4. The contour neighborhood region setting unit 231 sets the region A8 as a contour neighborhood region.

Figure 18A:
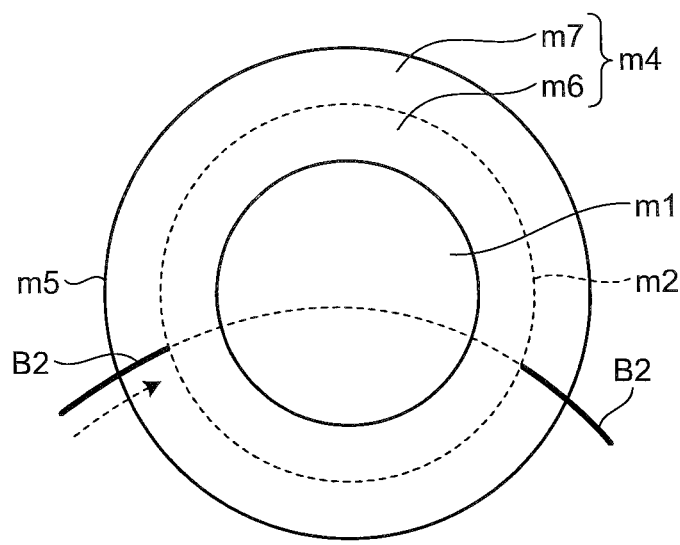
FIGS. 18A and 18B are schematic diagrams for illustrating a method for evaluating an intersection state of a blood vessel region with respect to a candidate region.
Figure 18B:
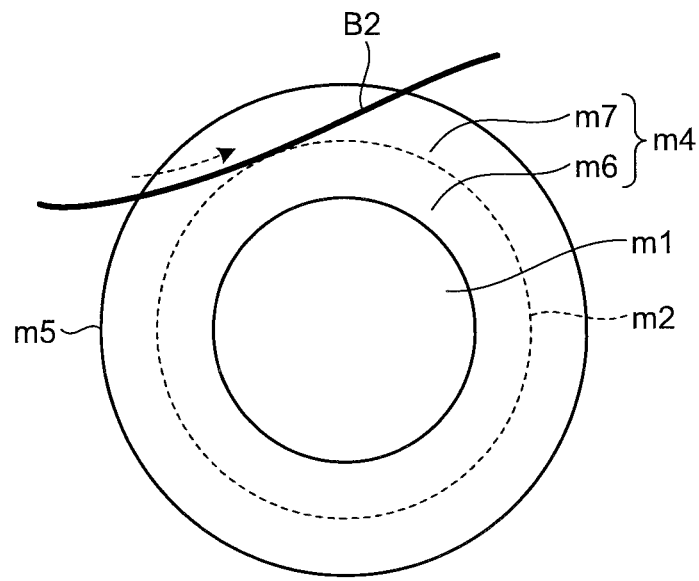

Subsequently, the abnormal region determination unit 230 executes loop-B processing for each of the candidate regions to which label numbers have been given. First, in step S232, the blood vessel intersection state evaluation unit 232 evaluates whether the blood vessel region intersects the contour of the candidate region and penetrates into the candidate region, for each of the blood vessel regions existing in the contour neighborhood region of the candidate region as a processing target, among the blood vessel regions extracted in step S131. FIGS. 18A and 18B are schematic diagrams for illustrating a method for evaluating an intersection state of a blood vessel region with respect to a candidate region.

The blood vessel intersection state evaluation unit 232 extracts a thin blood vessel B2 by performing thinning processing on each of the blood vessel regions within a contour neighborhood region m4. Note that details of thinning processing are similar to the case of the first embodiment (refer to FIG. 13).

The blood vessel intersection state evaluation unit 232 extracts the thin blood vessel B2 existing on an outer contour m5 of the contour neighborhood region m4, and tracks a thin blood vessel B2 within the contour neighborhood region m4 by searching 8-neighbor pixels on the thin blood vessel B2, starting from a portion on the contour m5. The blood vessel intersection state evaluation unit 232 then determines whether the thin blood vessel B2 intersects the contour m2 and penetrates into a region m6 inside of the contour m2.

For example, as illustrated in FIG. 18A, the thin blood vessel B2 intersects the contour m2 and penetrates into the region m6. In FIG. 18B, on the other hand, the thin blood vessel B2 abuts on the region m6 and extends toward a region m7 outside of the contour m2, not penetrating into the region m6 inside of the contour m2.

In subsequent step S233, the determination unit 233 counts the number of blood vessel regions (thin blood vessels B2) that intersect the contour m2 of the candidate region m1 and penetrate into the candidate region m1, and determines whether the number of the blood vessel regions is equal to or more than a predetermined number. If the number of the blood vessel regions that intersect the contour m2 of the candidate region m1 and penetrate into the candidate region m1 is equal to or more than the predetermined number (step S233: Yes), the determination unit 233 determines that the candidate region m1 as a processing target is the abnormal region (step S234). If the number of the blood vessel regions that intersect the contour m2 of the candidate region m1 and penetrate into the candidate region m1 is less than the predetermined number (step S233: No), the determination unit 233 determines that the candidate region m1 as a processing target is not the abnormal region (step S235).

After the loop-B processing has been performed for all the extracted candidate regions, operation of the computing unit returns to the main routine.

As described above, according to the second embodiment of the present invention, whether the candidate region is the abnormal region is determined on the basis of the number of blood vessel regions that intersect the contour of the candidate region and penetrate into the candidate region, as the extension information on the blood vessel region. Accordingly, it is possible to detect, with high accuracy, the abnormal region in which blood vessel sharpness is locally decreased.

Note that in the second embodiment, it is allowable to perform processing by restricting the thickness of the blood vessel region as an evaluation target, similarly to the modification 1-3.

In the second embodiment, as similarly to the modification 1-7, it is allowable to determine that the candidate region is the abnormal region if the number of the blood vessel regions that intersect the contour of the candidate region and penetrate into the candidate region is equal to or more than a predetermined ratio, with respect to the number of blood vessel regions existing within the contour neighborhood region.

Third Embodiment

Figure 19:
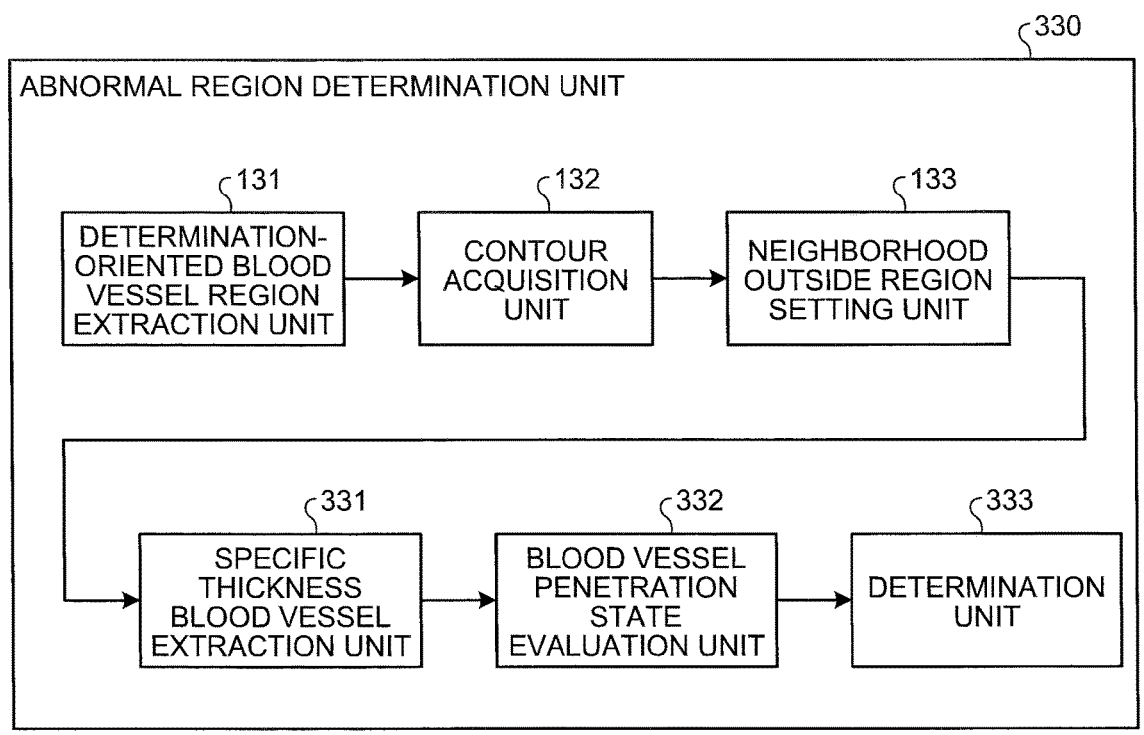
FIG. 19 is a block diagram illustrating a configuration of an abnormal region determination unit included in an image processing apparatus according to a third embodiment.

Next, a third embodiment of the present invention will be described. FIG. 19 is a block diagram illustrating a configuration of an abnormal region determination unit included in an image processing apparatus according to the third embodiment. The image processing apparatus according to the third embodiment includes an abnormal region determination unit 330 illustrated in FIG. 19 instead of the abnormal region determination unit 130 illustrated in FIG. 1 Configurations and operation of each of the units in the image processing apparatus are similar to the case of the first embodiment, except for the abnormal region determination unit 330.

The abnormal region determination unit 330 includes a determination-oriented blood vessel region extraction unit 131, a contour acquisition unit 132, a neighborhood outside region setting unit 133, a specific thickness blood vessel extraction unit 331, a blood vessel penetration state evaluation unit 332, and a determination unit 333. The determination-oriented blood vessel region extraction unit 131 extracts a blood vessel region to be used for determining whether the candidate region is an abnormal region, from the intraluminal image. The contour acquisition unit 132 obtains contour of the candidate region. The neighborhood outside region setting unit 133 sets a predetermined range of region outside of the contour of the candidate region, as a neighborhood outside region. The specific thickness blood vessel extraction unit 331 extracts blood vessel having a specific range of thickness, from the blood vessel region existing in the neighborhood outside region. The blood vessel penetration state evaluation unit 332 evaluates whether the blood vessel having the specific range of thickness penetrates the candidate region. The determination unit 333 determines whether the candidate region is the abnormal region on the basis of a result of evaluation performed by the blood vessel penetration state evaluation unit 332. Operation of the determination-oriented blood vessel region extraction unit 131, the contour acquisition unit 132, and the neighborhood outside region setting unit 133 are similar to the case of the first embodiment.

Next, operation of the image processing apparatus according to the third embodiment will be described. General operation of the image processing apparatus according to the third embodiment is similar to the case of the first embodiment (refer to FIG. 4), except for a difference in details of determination processing on the candidate region in step S13, from the first embodiment. In the third embodiment, the evaluation of whether the blood vessel region having a specific thickness penetrates the candidate region is used as the extension information on the blood vessel region.

Figure 20:
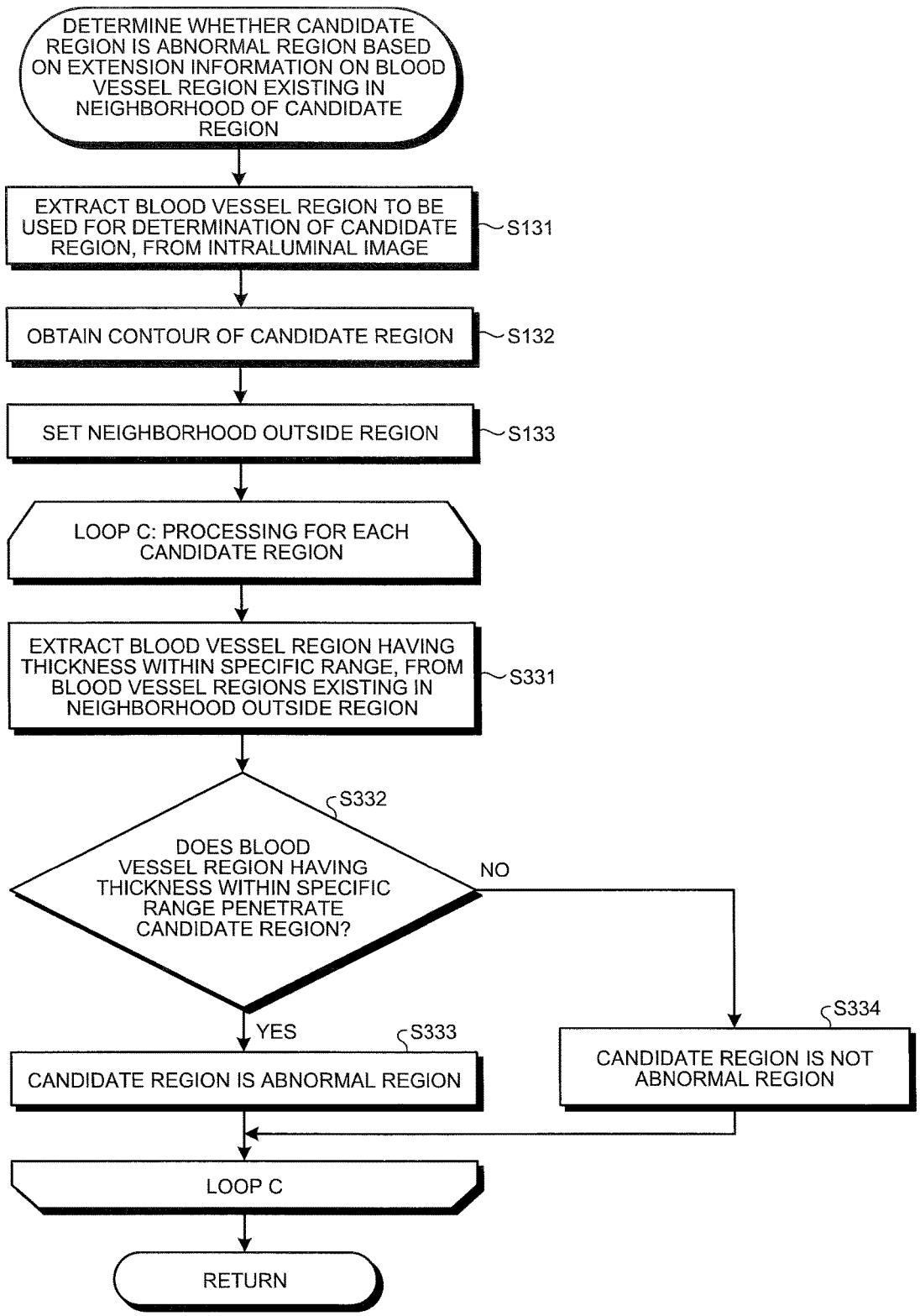
FIG. 20 is a flowchart illustrating processing of determining a candidate region, executed by the abnormal region determination unit illustrated in FIG. 19.

FIG. 20 is a flowchart illustrating processing of determining a candidate region, executed by the abnormal region determination unit 330 in step S13 illustrated in FIG. 4. Note that steps S131 and S133 illustrated in FIG. 20 are similar to the steps in the first embodiment.

Following step S133, the abnormal region determination unit 330 executes loop-C processing for each of the candidate regions to which label numbers have been given. First, in step S331, the specific thickness blood vessel extraction unit 331 extracts a blood vessel region having a specific range of thickness, from the blood vessel regions existing in the neighborhood outside region of the candidate region as a processing target, among the blood vessel regions extracted in step S131. As specific processing, the specific thickness blood vessel extraction unit 331 performs band-pass filter processing of a specific spatial frequency band, on the neighborhood outside region set to be the candidate region as a processing target. With this, the blood vessel region having a thickness corresponding to the specific spatial frequency band is extracted.

In subsequent step S332, the blood vessel penetration state evaluation unit 332 determines whether the blood vessel region having the specific range of thickness extracted in step S331 penetrates the candidate region. For simplicity, in a case where a plurality of blood vessel regions having the specific range of thickness exists within a same neighborhood outside region, the blood vessel region is determined to penetrate the candidate region.

Figure 21:
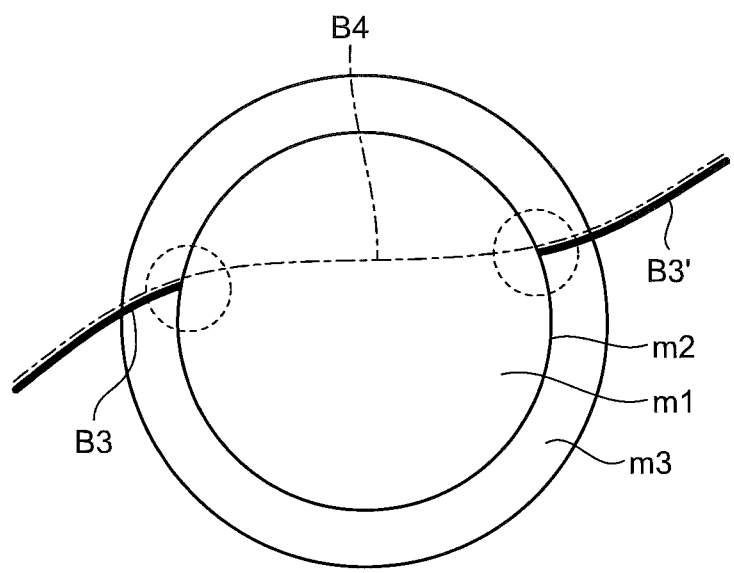
FIG. 21 is a schematic diagram for illustrating a method for evaluating a penetration state of a blood vessel region with respect to a candidate region.

FIG. 21 is a schematic diagram for illustrating a method for evaluating, with higher accuracy, a penetration state of a blood vessel region with respect to a candidate region. For performing evaluation with higher accuracy, the blood vessel penetration state evaluation unit 332 obtains thin blood vessels B3 and B3' by performing thinning processing on the blood vessel region having a specific range of thickness, extracted from the neighborhood outside region m3. Note that details of thinning processing are similar to the case of the first embodiment (refer to FIG. 13). Subsequently, an approximate curve B4 is created for the thin blood vessel B3, and whether the thin blood vessel exists within a predetermined range including the approximate curve B4, in the neighborhood outside region m3 opposite to where the thin blood vessel B3 is provided is determined. In the case of FIG. 21, a thin blood vessel B3' leading to the approximate curve B4 exists in the neighborhood outside region m3 opposite to where the thin blood vessel B3 exists. In this case, the blood vessel region that corresponds to the thin blood vessel B3 is determined to penetrate the candidate region and to be connected to the blood vessel region that corresponds to the thin blood vessel B3' existing in the opposite neighborhood outside region.

In a case where the blood vessel region having a specific range of thickness penetrates the candidate region m1 (step S332: Yes), the determination unit 333 determines that the candidate region m1 as a processing target is the abnormal region (step S333). In another case where the blood vessel region having the specific range of thickness does not penetrate the candidate region (step S332: No), the determination unit 333 determines that the candidate region m1 as a processing target is not the abnormal region (step S334).

After the loop-C processing has been performed for all the extracted candidate regions, operation of the computing unit returns to the main routine.

As described above, according to the third embodiment of the present invention, whether the candidate region is the abnormal region is determined on the basis of the evaluation of whether the blood vessel having a specific thickness penetrates the candidate region, as the extension information on the blood vessel region. Accordingly, it is possible to detect, with high accuracy, the abnormal region in which blood vessel sharpness is locally decreased.

Figure 22:
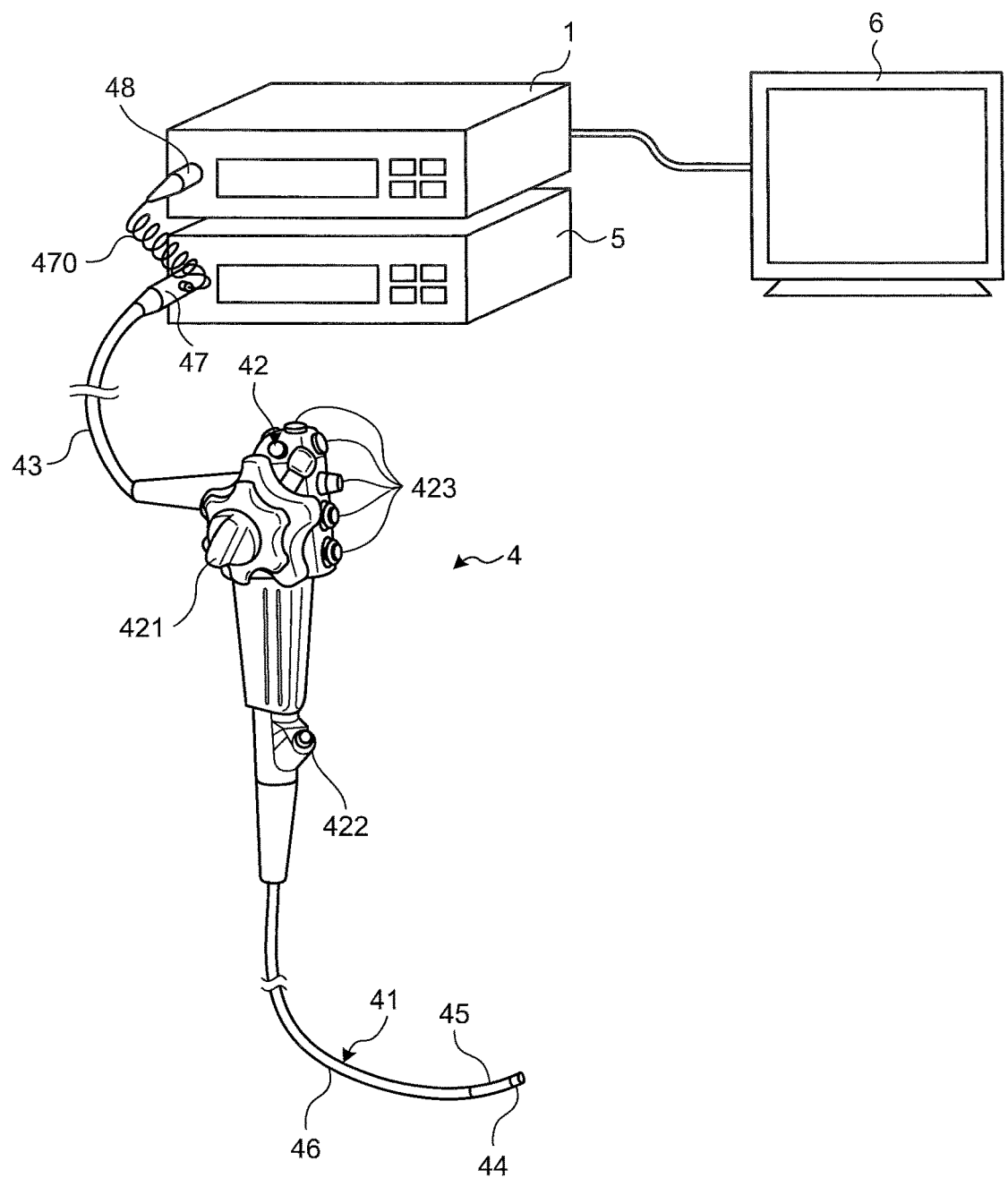
FIG. 22 is a diagram illustrating a general configuration of an endoscope system to which the image processing apparatus illustrated in FIG. 1 is applied.

FIG. 22 is a diagram illustrating a general configuration of an endoscope system to which the image processing apparatus (refer to FIG. 1) according to the first embodiment of the present invention is applied. An endoscope system 3 illustrated in FIG. 22 includes the image processing apparatus 1, an endoscope 4, a light source device 5, and a display device 6. The endoscope 4 generates an image obtained by imaging the inside of the body of a subject by inserting its distal end portion into the lumen of the subject. The light source device 5 generates illumination light to be emitted from the distal end of the endoscope 4. The display device 6 displays an in-vivo image image-processed by the image processing apparatus 1. The image processing apparatus 1 performs predetermined image processing on the image generated by the endoscope 4, and together with this, integrally controls general operation of the endoscope system 3. Note that it is also allowable to employ the image processing apparatus according to the second and third embodiments, instead of the image processing apparatus according to the first embodiment.

The endoscope 4 includes an insertion unit 41, an operating unit 42, and a universal cord 43. The insertion unit 41 is a flexible and elongated portion. The operating unit 42 is connected on a proximal end of the insertion unit 41 and receives input of various operation signals. The universal cord 43 extends from the operating unit 42 in a direction opposite to the extending direction of the insertion unit 41, and incorporates various cables for connecting with the image processing apparatus 1 and the light source device 5.

The insertion unit 41 includes a distal end portion 44, a bending portion 45, and a flexible needle tube 46. The distal end portion 44 incorporates an image element. The bending portion 45 is a bendable portion formed with a plurality of bending pieces. The flexible needle tube 46 is long and flexible portion connected with a proximal end of the bending portion 45.

The image element receives external light, photoelectrically converts the light, and performs predetermined signal processing. The image element is implemented with a charge coupled device (CCD) image sensor and a complementary metal oxide semiconductor (CMOS) image sensor.

Between the operating unit 42 and the distal end portion 44, a cable assembly is connected. This cable assembly includes a plurality of signal lines arranged in a bundle, to be used for transmission and reception of electrical signals with the image processing apparatus 1. The plurality of signal lines includes a signal line for transmitting a video signal output from the image element to the image processing apparatus 1, and a signal line for transmitting a control signal output from the image processing apparatus 1 to the image element.

The operating unit 42 includes a bending knob 421, a treatment instrument insertion section 422, and a plurality of switches 423. The bending knob 421 is provided for bending the bending portion 45 in up-down directions, and in left-right directions. The treatment instrument insertion section 422 is provided for inserting treatment instruments such as a biological needle, biological forceps, a laser knife, and an examination probe. The plurality of switches 423 is an operation input unit for inputting operating instruction signals for not only the image processing apparatus 1 and the light source device 5, but also for peripheral equipment including an air feeding apparatus, a water feeding apparatus, and a gas feeding apparatus.

The universal cord 43 incorporates at least a light guide and a cable assembly. Moreover, the end portion of the side differing from the side linked to the operating unit 42 of the universal cord 43 includes a connector unit 47 and an electrical connector unit 48. The connector unit 47 is removably connected with the light source device 5. The electrical connector unit 48 is electrically connected with the connector unit 47 via a coil cable 470 having a coil shape, and is removably connected with the image processing apparatus 1.

The image processing apparatus 1 generates an intraluminal image to be displayed by the display device 6, on the basis of the image signal output from the distal end portion 44. Specifically, the image processing apparatus 1 creates an intraluminal image for display by performing, for example, white balance (WB) adjustment processing, gain adjustment processing, γ correction processing, D/A conversion processing, and format change processing, on an image signal, and performs image processing of extracting an abnormal region from the above-described intraluminal image.

The light source device 5 includes a light source, a rotation filter, and a light source control unit, for example. The light source is configured with a white light-emitting diode (LED), a xenon lamp, or the like, and generates white light under the control of the light source control unit. The light generated from the light source is emitted from the tip of the distal end portion 44 via the light guide.

The display device 6 has a function of receiving an in-vivo image generated by the image processing apparatus 1 from the image processing apparatus 1 via the image cable and displaying the in-vivo image. The display device 6 is formed with, for example, liquid crystal, or organic electro luminescence (EL).

The above-described first to third embodiments and the modifications of the embodiments can be implemented by executing an image processing program recorded in a recording device on a computer system such as a personal computer and a workstation. Furthermore, such a computer system may be used by connecting the computer system to another device including a computer system or a server via a local area network (LAN), a wide area network (WAN), or a public line such as the Internet. In this case, it is allowable to configure such that the image processing apparatus according to the first to third embodiments and the modifications of the embodiments obtains image data of an intraluminal image via these networks, outputs a result of image processing to various output devices such as a viewer and a printer, connected through these networks, and stores results of image processing in a storage device connected via these networks, such as a recording medium and a reading device therefor.

According to some embodiments, a region in which sharpness of a blood vessel region is locally decreased in an intraluminal image is extracted as a candidate region for an abnormal region, and whether the candidate region is the abnormal region is determined based on extension information on the blood vessel region existing in a neighborhood of the candidate region. With this feature, it is possible to detect, with high accuracy, a region in which the visible vascular pattern is locally lost in the intraluminal image.

The present invention is not limited to the first to third embodiments and the modifications of the embodiments, but various inventions can be formed by appropriately combining a plurality of elements disclosed in the embodiments and the modifications. For example, the invention may be formed by removing some elements from all the elements described in each of the embodiments and the modifications, or may be formed by appropriately combining elements described in different embodiments and modifications.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An image processing apparatus comprising:
    a processor comprising hardware, wherein the processor is configured to:
        acquire an intraluminal image generated by capturing an image of a lumen of a subject;
        create a blood vessel sharpness image representing sharpness of a blood vessel region in which a blood vessel is shown in the intraluminal image;
        extract a region in which the sharpness is decreased in the blood vessel sharpness image, as a candidate region for an abnormal region in which a visible vascular pattern is locally lost; and
        determine whether the candidate region is an abnormal region, based on extension information indicating a state of the blood vessel region extending in a neighborhood of the candidate region.

2. The image processing apparatus according to claim 1, wherein the processor is configured to:
    set a detection target region for detecting the abnormal region;
    create a color contrast image in which as absorbance for hemoglobin absorption wavelength band in a lumen increases, luminance decreases in the detection target region;
    detect, as the blood vessel region, a region having a valley-shaped luminance change in the color contrast image; and
    calculate, as the sharpness, feature data representing a shape of the luminance change in the blood vessel region detected in the color contrast image.

3. The image processing apparatus according to claim 2, wherein based on color information and edge information in the intraluminal image, the processor is configured to set, as the detection target region, a region obtained by eliminating at least one of a mucosa contour, a dark portion, specular reflection, a bubble, and a residue, from the intraluminal image.

4. The image processing apparatus according to claim 1, wherein the processor is configured to:
    set a region outside of a contour of the candidate region, as a neighborhood outside region;
    evaluate whether an intersection angle between the blood vessel region existing in the neighborhood outside region and the contour of the candidate region falls within a predetermined range; and
    determine whether the candidate region is the abnormal region based on the number of blood vessel regions for which the intersection angle falls within the predetermined range.

5. The image processing apparatus according to claim 4, wherein the processor is configured to:
    perform thinning processing on the blood vessel region existing in the neighborhood outside region, thereby to obtain a thin blood vessel; and
    obtain, as the intersection angle, an angle between a direction of the thin blood vessel at an intersection of the thin blood vessel with the contour of the candidate region, and a normal direction of a tangent of the contour at the intersection.

6. The image processing apparatus according to claim 4, wherein the processor is configured to:
    perform thinning processing on the blood vessel region existing in the neighborhood outside region, thereby to obtain a thin blood vessel; and
    obtain, as the intersection angle, an angle between a direction of the thin blood vessel at an intersection of the thin blood vessel with the contour of the candidate region, and a tangent direction of the contour at the intersection.

7. The image processing apparatus according to claim 4, wherein the processor is configured to perform band-pass filter processing on the neighborhood outside region, and to perform evaluation for the blood vessel region extracted by the band-pass filter processing.

8. The image processing apparatus according to claim 1, wherein the processor is configured to:
set a predetermined range of region outside and inside a contour of the candidate region, as a contour neighborhood region;
evaluate whether the blood vessel region existing in the contour neighborhood region intersects the contour of the candidate region and penetrates into the candidate region; and
determine whether the candidate region is the abnormal region based on the number of blood vessel regions that intersect the contour of the candidate region and penetrate into the candidate region.

9. The image processing apparatus according to claim 8, wherein the processor is configured to:
perform thinning processing on the blood vessel region existing in the contour neighborhood region, thereby to obtain a thin blood vessel; and
track the thin blood vessel starting from an outer contour of the contour neighborhood region into the contour neighborhood region, thereby to evaluate whether the thin blood vessel intersects the contour of the candidate region and penetrates into the contour neighborhood region inside the contour.

10. The image processing apparatus according to claim 8, wherein the processor is configured to perform band-pass filter processing on the contour neighborhood region, and to perform evaluation for the blood vessel region extracted by the band-pass filter processing.

11. The image processing apparatus according to claim 1, wherein the processor is configured to:
set a region outside a contour of the candidate region as a neighborhood outside region;
extract a blood vessel region having a specific range of thickness, from the blood vessel region existing in the neighborhood outside region;
evaluate whether the blood vessel region having the specific range of thickness penetrates the candidate region; and
determine that the candidate region is the abnormal region if the blood vessel region having the specific range of thickness penetrates the candidate region.

12. The image processing apparatus according to claim 11,
wherein if a plurality of blood vessel regions having the specific range of thickness exists in the neighborhood outside region, the processor is configured to, evaluate that the blood vessel regions having the specific range of thickness penetrate the candidate region.

13. The image processing apparatus according to claim 11,
wherein the processor is configured to:
perform thinning processing on the blood vessel region having the specific range of thickness, thereby to obtain a thin blood vessel; and
evaluate that the blood vessel region having the specific range of thickness penetrates the candidate region if an additional thin blood vessel exists in the neighborhood outside region opposite to where the thin blood vessel exists, the additional thin blood vessel existing within a predetermined range having an approximate curve created for the thin blood vessel.

14. An image processing method, comprising:
acquiring an intraluminal image generated by capturing an image of a lumen of a subject;
creating a blood vessel sharpness image representing sharpness of a blood vessel region in which a blood vessel is shown in the intraluminal image;
extracting a region in which the sharpness is decreased in the blood vessel sharpness image, as a candidate region for an abnormal region in which a visible vascular pattern is locally lost; and
determining whether the candidate region is an abnormal region, based on extension information indicating a state of the blood vessel region extending in a neighborhood of the candidate region.

15. A non-transitory computer-readable recording medium with an executable program stored thereon, the program causing a computer to execute:
acquiring an intraluminal image generated by capturing an image of a lumen of a subject;
creating a blood vessel sharpness image representing sharpness of a blood vessel region in which a blood vessel is shown in the intraluminal image;
extracting a region in which the sharpness is decreased in the blood vessel sharpness image, as a candidate region for an abnormal region in which a visible vascular pattern is locally lost; and
determining whether the candidate region is an abnormal region, based on extension information indicating a state of the blood vessel region extending in a neighborhood of the candidate region.

* * * * *